(12) United States Patent
Ray et al.

(10) Patent No.: US 9,491,942 B2
(45) Date of Patent: Nov. 15, 2016

(54) METHODS FOR ASSESSING REPELLANT QUALITY OF ORGANIC MATERIALS AND METHODS AND COMPOSITIONS FOR REPELLING ARTHROPODS

(71) Applicant: The Regents of the University of California, Oakland, CA (US)

(72) Inventors: Anandasankar Ray, Riverside, CA (US); Sean Michael Boyle, Lakewood Ranch, FL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/352,483

(22) PCT Filed: Oct. 17, 2012

(86) PCT No.: PCT/US2012/060673
§ 371 (c)(1),
(2) Date: Apr. 17, 2014

(87) PCT Pub. No.: WO2013/059364
PCT Pub. Date: Apr. 25, 2013

(65) Prior Publication Data
US 2015/0126437 A1    May 7, 2015

Related U.S. Application Data

(60) Provisional application No. 61/548,141, filed on Oct. 17, 2011.

(51) Int. Cl.
| | |
|---|---|
| *A01N 37/18* | (2006.01) |
| *C08G 16/02* | (2006.01) |
| *A01N 37/44* | (2006.01) |
| *A01N 43/60* | (2006.01) |
| *A01N 43/54* | (2006.01) |
| *A01N 47/46* | (2006.01) |
| *A01N 47/42* | (2006.01) |
| *A01N 43/90* | (2006.01) |
| *A01N 43/78* | (2006.01) |
| *A01N 43/32* | (2006.01) |
| *A01N 37/20* | (2006.01) |
| *A01N 37/22* | (2006.01) |
| *A01N 43/42* | (2006.01) |
| *A01N 37/46* | (2006.01) |
| *A01N 43/50* | (2006.01) |
| *A01N 35/10* | (2006.01) |
| *A01N 33/10* | (2006.01) |
| *A01N 43/38* | (2006.01) |
| *A01N 31/02* | (2006.01) |
| *A01N 35/06* | (2006.01) |
| *A01N 37/36* | (2006.01) |
| *A01N 43/40* | (2006.01) |
| *A01N 47/16* | (2006.01) |

(52) U.S. Cl.
CPC .............. *A01N 37/44* (2013.01); *A01N 31/02* (2013.01); *A01N 33/10* (2013.01); *A01N 35/06* (2013.01); *A01N 35/10* (2013.01); *A01N 37/18* (2013.01); *A01N 37/20* (2013.01); *A01N 37/22* (2013.01); *A01N 37/36* (2013.01); *A01N 37/46* (2013.01); *A01N 43/32* (2013.01); *A01N 43/38* (2013.01); *A01N 43/40* (2013.01); *A01N 43/42* (2013.01); *A01N 43/50* (2013.01); *A01N 43/54* (2013.01); *A01N 43/60* (2013.01); *A01N 43/78* (2013.01); *A01N 43/90* (2013.01); *A01N 47/16* (2013.01); *A01N 47/42* (2013.01); *A01N 47/46* (2013.01)

(58) Field of Classification Search
None
See application file for complete search history.

(56) References Cited

U.S. PATENT DOCUMENTS

| | | |
|---|---|---|
| 5,089,469 A | 2/1992 | Zampino et al. |
| 5,175,175 A | 12/1992 | Wilson et al. |
| 5,354,783 A | 10/1994 | Marin et al. |
| 6,267,953 B1 | 7/2001 | Bernier et al. |
| 6,372,804 B1 | 4/2002 | Ikemoto et al. |
| 6,719,959 B1 | 4/2004 | Gonzalez et al. |
| 6,800,279 B2 | 10/2004 | Bernier et al. |
| 6,958,146 B2 | 10/2005 | Askham et al. |
| 7,867,479 B2 | 1/2011 | Dunham et al. |
| 8,048,683 B2 | 11/2011 | Grau et al. |
| 8,092,790 B2 | 1/2012 | Dunham et al. |
| 8,945,595 B2 | 2/2015 | Ray et al. |
| 2002/0028191 A1 | 3/2002 | Bernier et al. |
| 2004/0223998 A1 | 11/2004 | Iyer et al. |
| 2004/0242699 A1 | 12/2004 | Askham et al. |

(Continued)

FOREIGN PATENT DOCUMENTS

| | | |
|---|---|---|
| CN | 1809368 A | 7/2006 |
| JP | 2000-290104 A | 10/2000 |

(Continued)

OTHER PUBLICATIONS

Weeks et al. Army Environ. Hyg. Agency, Aberdeen Proving Ground, MD, USA, Hazard evaluation program of candidate insect repellent A13-36706 pentyl 2-aminobenzoate, From: Gov. Rep. Announce. Index (U. S.) 1977, 77(19), 97.*
PubChem (Pentyl-2 aminobenzoate, Mar. 26, 2005 CID 100495.*
Carey et al., "Odorant Reception in the Malaria Mosquito Anopheles Gambiae", Nature, 2010, pp. 1-7.
Hallem et al., "Coding of Odors by a Receptor Repertoire", Cell, vol. 125, Apr. 7, 2006, pp. 143-160.

(Continued)

*Primary Examiner* — Jeanette Lieb
(74) *Attorney, Agent, or Firm* — Morrison & Foerster LLP

(57) ABSTRACT

The disclosure provides compounds useful as insect repellents, compositions comprising such repellents, and methods of repelling an arthropod using such compounds and compositions. The disclosure further provides insect traps and method for identifying ligands and cognates for biological molecules.

28 Claims, 18 Drawing Sheets

(56) References Cited

U.S. PATENT DOCUMENTS

| | | |
|---|---|---|
| 2005/0008714 A1 | 1/2005 | Enan |
| 2006/0189690 A1 | 8/2006 | Dunham et al. |
| 2006/0193881 A1 | 8/2006 | Bedoukian |
| 2007/0142795 A1 | 6/2007 | Cohen et al. |
| 2007/0157323 A1 | 7/2007 | Carlson et al. |
| 2009/0047379 A1 | 2/2009 | Dewis et al. |
| 2009/0148398 A1 | 6/2009 | Vander Meer et al. |
| 2009/0176229 A1 | 7/2009 | Tracey, Jr. et al. |
| 2009/0196838 A1 | 8/2009 | Gupta et al. |
| 2010/0074972 A1 | 3/2010 | Rouseff et al. |
| 2010/0144888 A1 | 6/2010 | Bessette |
| 2010/0247684 A1 | 9/2010 | Reid et al. |
| 2011/0244056 A1 | 10/2011 | Santra |
| 2011/0263585 A1 | 10/2011 | Bernasconi et al. |
| 2012/0015841 A1 | 1/2012 | Shekdar et al. |
| 2013/0236417 A1 | 9/2013 | Ray et al. |
| 2015/0223458 A1 | 8/2015 | Ray et al. |

FOREIGN PATENT DOCUMENTS

| | | |
|---|---|---|
| WO | 98/23150 A1 | 6/1998 |
| WO | 00/065910 A1 | 11/2000 |
| WO | 2007/056043 A2 | 5/2007 |
| WO | 2011040252 A1 | 4/2011 |
| WO | 2012/018153 A1 | 2/2012 |
| WO | 2013/059364 A2 | 4/2013 |

OTHER PUBLICATIONS

Katritzky et al., "Synthesis and Bioassay of Improved Mosquito Repellents Predicted from Chemical Structure", PNAS, vol. 105, No. 21, May 27, 2008, pp. 7359-7364.

International Preliminary Report on Patentability received for PCT Patent Application No. PCT/US2012/060673, mailed on May 1, 2014, 7 pages.

Schmuker et al., "Predicting Olfactory Receptor Neuron Responses from Odorant Structure", Chemistry Central Journal, vol. 1, No. 11, 2007, pp. 1-10.

Syed et al., "Mosquitoes Smell and Avoid the Insect Repellent DEET", PNAS, vol. 105, No. 36, Sep. 9, 2008, pp. 13598-13603.

International Search Report and Written Opinion received for PCT Patent Application No. PCT/US2012/060673, mailed on Apr. 1, 2013, 11 pages.

Extended European Search Report and European Search Opinion received for European Patent Application No. 10749292.8, mailed on Apr. 2, 2013, 7 pages.

Final Office Action received for U.S. Appl. No. 12/398,164, mailed on Apr. 16, 2014, 17 pages.

Final Office Action received for U.S. Appl. No. 12/398,164, mailed on Apr. 20, 2012, 10 pages.

Non Final Office Action received for U.S. Appl. No. 12/398,164, mailed on Aug. 12, 2013, 12 pages.

Non Final Office Action received for U.S. Appl. No. 12/398,164, mailed on Jun. 23, 2011, 10 pages.

Notice of Allowance received for U.S. Appl. No. 12/398,164, mailed on Sep. 26, 2014, 11 pages.

Partial Supplementary European Search Report received for European Patent Application No. 12841890.2 mailed on Jun. 11, 2015, 11 pages.

Non-Final Office Action received for U.S. Appl. No. 13/641,065, mailed on Aug. 15, 2014, 9 pages.

Bar-Zeev et al., "The Response of the Adults of the Khapra Beetle Trogoderma Granarium Everts (Coleoptera, Dermestidae) to Various Synthetic Compounds", Rivista Di Parassitologia, vol. XL, No. 1/2, 1979, pp. 49-55.

Benton et al., "Variant Ionotropic Glutamate Receptors as Chemosensory Receptors in Drosophila", Cell, vol. 136, No. 1, Jan. 9, 2009, pp. 149-162.

Boeckh et al., "Acylated 1,3-Aminopropanols as Repellents against Bloodsucking Arthropods", Pesticide Science, vol. 48, 1996, pp. 359-373.

Burton, D. J., "Intrinsic Mosquito Repellency Values of Some Chemical Compounds", American Perfumer and Cosmetics, vol. 84, Apr. 1969, pp. 41-44.

Dekker et al., "Identification of Mosquito Repellent Odours from Ocimum Forskolei", Parasites & Vectors, vol. 4, No. 183, 2011, pp. 1-7.

Douglas, III et al., "Chemical Odorant of Colonial Seabird Repels Mosquitoes", Journal of Medical Entomology, vol. 42, No. 4, Jul. 2005, pp. 647-651.

Gutierrez-Osuna, Ricardo, "Pattern Analysis for Machine Olfaction: A Review", IEEE Sensors Journal, vol. 2, No. 3, Jun. 2002, pp. 189-202.

Ihndris et al., "Effect of Promising Insect Repellents on Plastics and Paints", Database Accession No. "1955:86558", 1955, 2 pages.

Jones et al., "Two Chemosensory Receptors together Mediate Carbon Dioxide Detection in Drosophila", Nature, vol. 445, Jan. 4, 2007, pp. 86-90.

Jones, Walton, "Olfactory Carbon Dioxide Detection by Insects and Other Animals", Molecules and Cells, vol. 35, Issue 2, Feb. 28, 2013, pp. 87-92.

Kovalenko et al., "Repellent Properties of Mannich Bases Derived from Hydroxy and Aminobenzoic Acid Esters", Database Accession No. "1983:535492", 1983, 2 pages.

Linduska et al., "Flea Repellents for Use on Clothing", Journal of Economic Entomology, vol. 39, No. 6, Dec. 1946, pp. 767-769.

Lu et al., "Odor Coding in the Maxillary Palp of the Malaria Vector Mosquito Anopheles Gambiae", Current Biology, vol. 17, Sep. 18, 2007, pp. 1533-1544.

Mann et al., "Sulfur Volatiles from Allium Spp. affect Asian Citrus Psyllid, Diaphorina Citri Kuwayama (Hemiptera: Psyllidae), Response to Citrus Volatiles", Bulletin of Entomological Research, vol. 101, No. 1, Feb. 2011, pp. 89-97.

Paluch et al., "Mosquito Repellents: A Review of Chemical Structural Diversity and Olfaction", Pest Management Science, vol. 66, 2010, pp. 925-935.

Patt et al., "Responses of the Asian Citrus Psyllid to Volatiles Emitted by the Flushing Shoots of Its Rutaceous Host Plants", Environmental Entomology, vol. 39, No. 2, Apr. 2010, pp. 618-624.

International Preliminary Report on Patentability received for PCT Patent Application No. PCT/US2010/026108, mailed on Sep. 15, 2011, 8 pages.

International Search Report and Written Opinion received for PCT Patent Application No. PCT/US2010/026108, mailed on Oct. 19, 2010, 12 pages.

International Preliminary Repoprt on Patentability received for PCT PAtent Application No. PCT/US2011/032804, mailed on Oct. 26, 2012, 9 pages.

International Search Report received for PCT Patent Application No. PCT/US2011/032804, mailed on Dec. 26, 2011, 5 pages.

International Written Opinoin received for PCT Patent Application No. PCT/US2011/032804, mailed on Dec. 26, 2011, 7 pages.

International Preliminary Report on Patentability received for PCT Patent Application No. PCT/US2012/060130, mailed on Apr. 24, 2014, 9 pages.

International Search Report and Written Opinion received for PCT Patent Application No. PCT/US2012/060130, mailed on Mar. 18, 2013, 13 pages.

International Search Report and Written Opinion received for PCT Patent Application No. PCT/US2014/029201, mailed on Oct. 7, 2014, 5 pages.

Invitation to Pay Additional Fees received for PCT Patent Application No. PCT/US2014/029201, mailed on Jul. 24, 2014, 2 pages.

International Search Report and Written Opinion received for PCT Patent Application No. PCT/US2014/029524, mailed on Aug. 11, 2014, 5 pages.

Praag et al., "Steam Volatile Aroma Constituents of Roasted Cocoa Beans", Journal of Agricultural and Food Chemistry, vol. 16, No. 6, Nov. 1968, pp. 1005-1008.

Saito et al., "Odor Coding by a Mammalian Receptor Repertoire", Science Signaling, vol. 2, No. 60, Mar. 3, 2009, 28 pages.

Singer, Allen W., "Topical Hazard Evaluation Program of Candidate Insect", Database Accession No. 1980:141441, 1979, 2 pages.

(56) References Cited

OTHER PUBLICATIONS

Smagghe et al., "Insect Cell Culture and Applications to Research and Pest Management", In Vitro Cellular & Developmental Biology—Animal, vol. 45, Issue 3, Apr. 2009, pp. 93-105.
Smith et al., "Effectiveness of Repellents Applied to Clothing for Protection against Salt-Marsh Mosquitoes", Journal of Economic Entomology, vol. 42, 1949, 4 pages.
Svirbely et al., "Physical Properties of Some Organic Insect Repellents", Journal of The American Chemical Society, vol. 71, No. 2, Feb. 1949, pp. 507-509.
Viktorov-Nabokov et al., "Effect of Substituents in a Series of Benzoic Acid Esters and Amides on Repellence with respect to Blood-Sucking Mosquitoes", Fiziologicheski Aktivnye Veshchestva vol. 12, 1980, 1 page (Abstract only).
Weeks et al., "Topical Hazard Evaluation Program of Candidate Insect Repellent", Database Accession No. "1978:1227", 1977, 2 pages.
"Chemical Products Catalog (Shanghai)", Scientific and Technical Information Research Institute of Bureau of Chemical Industry, Shanghai, Feb. 1992, pp. 177, 180 & 450. (See Communication under 37 CFR § 1.98(a) (3)).
"Organic Synthesis, vol. III", E.C.Horning, Science Press, Aug. 31, 1981, pp. 435. (See Communication under 37 CFR § 1.98(a) (3)).
Ibrahim et al., "Toxicity and Inhibition of Feeding and Tunneling Response of Naphthalene and 10 Derivatives on the Formosan Subterranean Termite (Isoptera Rhinotermitidae)", Journal of Economic Entomology, vol. 103, Issue 6, Dec. 2010, pp. 2132-2139.
Extended European Search Report received for European Patent Application No. 12841890.2, mailed Oct. 19, 2015, 33 pages.
Notice of Allowance received for U.S. Appl. No. 14/540,908, mailed on Dec. 4, 2015, 8 pages.
Office Action received for Chinese Patent Application No. 201280059913.X, mailed on Feb. 26, 2016, 25 pages (14 pages of English Translation and 11 pages of Official Copy).
Abramson et al., "Proboscis Conditioning Experiments with Honeybees, Apis Mellifera Caucasica, with Butyric Acid and DEET Mixture as Conditioned and Unconditioned Stimuli", Journal of Insect Science, vol. 10, Article 122, 2010, pp. 1-17.
Abuin et al., "Functional Architecture of Olfactory Ionotropic Glutamate Receptors", Neuron, vol. 69, No. 1, Jan. 13, 2011, pp. 44-60.
Al et al., "Acid Sensing by the Drosophila Olfactory System", Nature, vol. 468, Dec. 2010, pp. 691-695.
Andreev K.P., "New Insect Repellents for Protection of Humans and Animals from Bloodsucking Flies, Mosquitoes, Midges, and Gnats", Chemical Abstracts Service, Columbus, Ohio, US; 1958,XP002744302, Database accession No. 1960:64502.
Office Action received for African Regional Patent Application No. AP/P/2012/006552, mailed on Jul. 6, 2015, 6 pages.
Bernier et al., "Analysis of Human Skin Emanations by Gas. Chromatography/Mass Spectrometry. 1. Thermal Desportion of Attractants for the Yellow Fever Mosquito (Aedes aegypti) from Handled Glass Beads", Analytical Chemistry, vol. 71, No. 1, Jan. 1, 1999, pp. 1-7.
Bernier et al., "Analysis of Human Skin Emanations by Gas Chromatography/Mass Spectrometry. 2. Identification of Volatile Compounds That Are Candidate Attractants for the Yellow Fever Mosquito (Aedes aegypti)", Analytical Chemistry, vol. 72, No. 4, Feb. 15, 2000, pp. 747-756.
Bohbot et al., "Selectivity of Odorant Receptors in Insects", Frontiers in Cellular Neuroscience, vol. 6, Article 29, Jul. 2012, pp. 1-4.
Braks et al., "Infochemicals in Mosquito Host Selection: Human Skin Microflora and Plasmodium Parasites", Parasitology Today, vol. 15, No. 10, 1999, pp. 409-413.
Bruyne et al., "Odor Coding in a Model Olfactory Organ: The Drosophila Maxillary Palp", The Journal of Neuroscience, vol. 19, No. 11, Jun. 1, 1999, pp. 4520-4532.
Butler, Declan, "Mosquitoes Score in Chemical War", Nature, vol. 475, Jul. 7, 2011, p. 19.

Cardéet al., "Host Finding by Female Mosquitoes: Mechanisms of Orientation to Host Odours and other Cues", Olfaction in Vector-Host Interactions, 2010, pp. 115-141.
Cardéet al., "Navigational Strategies used by Insects to find Distant, Wind-Borne Sources of Odor", Journal of Chemical Ecology, vol. 34, 2008, pp. 854-866.
Chang et al., "LIBSVM: A Library for Support Vector Machines", LIBSVM, 2001, pp. 1-39.
Chiang et al., "Three-Dimensional Reconstruction of Brain-wide Wiring Networks in Drosophila at Single-Cell Resolution", Current Biology, vol. 21, Jan. 11, 2011, pp. 1-11.
Cook et al., "The Use of Push-Pull Strategies in Integrated Pest Management", Annual Review of Entomology, vol. 52, 2007, pp. 375-400.
Cooperband et al., "Orientation of Culex Mosquitoes to Carbon Dioxidebaited Traps: Flight Manoeuvres and Trapping Efficiency", Medical and Veterinary Entomology, vol. 20, 2006, pp. 11-26.
Corbel et al., "Evidence for Inhibition of Cholinesterases in Insect and Mammalian Nervous Systems by the Insect Repellent Deet", BMC Biology, vol. 7, 2009, pp. 1-11.
Cortes et al., "Support-Vector Networks", Machine Learning, vol. 20, 1995, pp. 273-297.
Croset et al., "Ancient Protostome Origin of Chemosensory Ionotropic Glutamate Receptors and the Evolution of Insect Taste and Olfaction", PLoS Genetics, vol. 6, Issue 8, Aug. 2010, pp. 1-20.
Curran et al., "Comparison of the Volatile Organic Compounds Present in Human Odor Using SPME-GC/MS", Journal of Chemical Ecology, vol. 31, No. 7, Jul. 2005, pp. 1607-1619.
Dekker et al., "Carbon Dioxide Instantly Sensitizes Female Yellow Fever Mosquitoes to Human Skin Odours", The Journal of Experimental Biology, vol. 208, 2005, pp. 2963-2972.
Dekker, et al., "Moment-to-moment Flight Manoeuvres of the Female Yellow Fever Mosquito (Aedes Aegypti L.) in Response to Plumes of Carbon Dioxide and Human Skin Odour", The Journal of Experimental Biology, vol. 214, 2011, pp. 3480-3494.
Dekker et al., "Structure of Host-Odour Plumes Influences Catch of Anopheles Gambiae S.S. and Aedes Aegypti in a Dualchoice Olfactometer", Physiological Entomology, vol. 26, 2001, pp. 124-134.
Ditzen et al., "Insect Odorant Receptors Are Molecular Targets of the Insect Repellent DEET", Science, vol. 319, 2008, pp. 1838-1842.
Erdelyan et al., "Functional Validation of the Carbon Dioxide Receptor Genes in Aedes Aegypti Mosquitoes using RNA Interference", Insect Molecular Biology, vol. 21, No. 1, 2012, pp. 119-127.
Gallagher et al., "Analyses of Volatile Organic Compounds from Human Skin", British Journal of Dermatology, vol. 159, No. 4, 2008, pp. 780-791.
Ghaninia et al., "Natural Odor Ligands for Olfactory Receptor Neurons of the Female Mosquito Aedes Aegypti: Use of Gas Chromatography-linked Single Sensillum Recordings", The Journal of Experimental Biology, vol. 211, 2008, pp. 3020-3027.
Gillies, M. T., "The role of Carbon Dioxide in Host-Finding by Mosquitoes.(Diptera: Culicidae): A Review", Bulletin of Entomological Research, vol. 70, 1980, pp. 525-532.
Haasen et al., "Pharmacological Profiling of Chemokine Receptor—Directed Compounds Using High-Content Screening", Journal of Biomolecular Screening, vol. 13, No. 1, 2008, pp. 40-53.
Haddad et al., "A Metric for Odorant Comparison", Nature Methods, vol. 5, 2008, pp. 1-5.
Halbert et al., "Plant-Derived Compounds and Extracts with Potential as Aphid Repellents", Annals of Applied Biology, vol. 154, No. 2, 2009, pp. 303-307.
Hawkins, et al., "Conformer Generation with Omega: Algorithm and Validation Using High Quality Structures from the Protein Databank and Cambridge Structural Database", Journal of Chemical Information and Modeling, vol. 50, No. 4, 2010, pp. 572-584.
Hayes, J. L., "Identification of a Host Compound and its Practical Applications: 4-Aiiylanisole as a Bark Beetle Repellent", Chemical Abstracts Service, 1994, pp. 69-79.
Hou et al., "The Effect of Repellents on Penetration into Packaging by Stored-Product Insects", Journal of Stored Research, vol. 40, 2004, pp. 47-54.

(56) References Cited

OTHER PUBLICATIONS

Hwang et al., "Isolation and Identification of Mosquito Repellents in Artemisia Vulgaris", Journal of Chemical Ecology, vol. 11, Issue 9, Sep. 1985, pp. 1297-1306.
Innocent Ester et al., "Constituents of the Essential Oil of Suregada Zanzibariensis Leaves are S.S", Journal of Insect Science, vol. 10, Article 57, 2010, pp. 1-8.
Jawara et al., "Field Testing of Different Chemical Combinations as Odour Baits for Trapping Wild Mosquitoes in the Gambia", Plos One, vol. 6, Issue 5, 2011, pp. 1-7.
Gaudin et al., "Carboxamides combining Favorable Olfactory Properties with Insect Repellency", Chemistry & Biodiversity, vol. 5, No. 4, Apr. 2008, pp. 617-635.
Jones et al., "Allosteric Antagonism of Insect Odorant Receptor Ion Channels", Plos One, vol. 7, Issue 1, Jan. 2012, pp. 1-7.
Kao et al., "The Biochemical basis for the Anti-inflammatory and Cytoprotective Actions of Ethyl Pyruvate and Related Compounds", Biochemical Pharmacology, vol. 80, 2010, pp. 151-159.
Karatzoglou et al., "Support Vector Machines in R", Journal of Statistical Software, vol. 15, Issue 9, Apr. 2006, pp. 1-28.
Kline et al., "Olfactometric Evaluation of Spatial Repellents for Aedes Aegypti", Journal of Medical Entomology, vol. 40, No. 4, 2003, pp. 463-467.
Klun et al., "Comparative Resistance of Anopheles Albimanus and Aedes Aegypti to N,N-Diethyl-3-Methylbenzamide (Deet) and 2-Methylpiperidinyl-3-Cyclohexen-1-Carboxamide (AI3-37220) in Laboratory Human—Volunteer Repellent Assays", Journal of Medical Entomology, vol. 41, No. 3, May 2004, pp. 418-422.
Knudsen et al., "Diversity and Distribution of Floral Scent", The Botanical Review, vol. 72, No. 1, 2006, pp. 1-120.
Leal et al., "Medicinal Alkaloid as a Sex Pheromone", Nature, vol. 385, Jan. 1997, p. 213.
Lee et al., "Avoiding DEET through Insect Gustatory Receptors", Neuron, vol. 67, No. 4, 2010, pp. 555-561.
Mackay et al., "The *Drosophila Melanogaster* Genetic Reference Panel", Nature, vol. 482, Feb. 9, 2012, pp. 173-178.
Masuyama et al., "Mapping Neural Circuits with Activity-Dependent Nuclear Import of a Transcription Factor", Journal of Neurogenetics, vol. 26, No. 1, 2012, pp. 89-102.
Mayer, D. F., "Field Evaluation of Non-Pesticide Chemicals as Honey Bee Repellents", Chemical Abstracts Service, Columbus, Ohio, US; 2001, XP002744301, Database accession No. 2001:493021.
Mumcuoglu et al., "Repellency of Essential Oils and their Components to the Human Body Louse, Pediculus Humanus Humanus", Entomologia Experimentalis et Applicata, vol. 78, pp. 309-314.
Nikonov et al., "A Photoaffinity-Labeled Green Leaf Volatile Compound 'Tricks'Highly Selective and Sensitive Insect Olfactory Receptor Neurons", Chemical Senses, vol. 26, 2001, pp. 49-54.
Njiru et al., "Trapping of the Malaria Vector Anopheles Gambiae with Odour-baited MM-X Traps in Semi- field Conditions in Western Kenya", Malaria Journal, vol. 5, 2006, pp.1-8.
International Preliminary Report on Patentability received for PCT Patent Application No. PCT/US2014/029201, mailed on Sep. 24, 2015, 8 pages.
International Preliminary Report on Patentability received for PCT Patent Application No. PCT/US2014/029524, mailed on Sep. 24, 2015, 9 pages.
Pellegrino et al., "A Natural Polymorphism Alters Odour and DEET Sensitivity in an Insect Odorant Receptor", Nature, vol. 478, No. 7370, Sep. 2011, pp. 511-514.
Pitts et al., "Transcriptome Profiling of Chemosensory Appendages in the Malaria Vector Anopheles Gambiae Reveals Tissue—and Sex-specific Signatures of Odor Coding", BMC Genomics, vol. 12, No. 271, 2011, pp. 1-17.
Qiu et al., "Attractiveness of MM-X Traps Baited with Human or Synthetic Odor to Mosquitoes (Diptera: Culicidae) in the Gambia", Journal of Medical Entomology, vol. 44, No. 6, Nov. 2007, pp. 970-983.
Qiu et al., "Olfactory Coding in Antennal Neurons of th Malaria Mosquito, Anopheles Gambiae", Chem. Senses, vol. 31, 2006, pp. 845-863.
Rámia et al., "PopDrowser: the Population Drosophila Browser", Bioinformatics, vol. 28, No. 4, 2012, pp. 595-596.
Ramirez et al., "Repellents Inhibit P450 Enzymes in Stegomyia (Aedes) Aegypti", Plos One, vol. 7, Issue 11, Nov. 2012, pp. 1-8.
Rehr et al., "L-Dopa in Legume Seeds: A Chemical Barrier to Insect Attack", Science, vol. 181, Issue 4094, Jul. 1973, pp. 81-82.
Robertson et al., "Evolution of the Gene Lineage Encoding the Carbon Dioxide Receptor in Insects", Journal of Insect Science, vol. 9, Article 19, 2009, pp. 1-14.
Silbering et al., "Complementary Function and Integrated Wiring of the Evolutionarily Distinct Drosophila Olfactory Subsystems", The Journal of Neuroscience, vol. 31, No. 38, Sep. 21, 2011, pp. 13357-13375.
Smallegange et al., "Effectiveness of Synthetic Versus Natural Human Volatiles as Attractants for Anopheles Gambiae (Diptera: Culicidae) Sensu Stricto", Journal of Medical Entomology, vol. 47, No. 3, May 2010, pp. 338-344.
Smallegange et al., "Host-seeking Behaviour of Mosquitoes: Responses to Olfactory Stimuli in the Laboratory", Olfaction in Vector-Host Interactions, Ch. 7, 2010, pp. 143-180.
Smallegange et al., "Synergism Between Ammonia, Lactic Acid and Carboxylic Acids as Kairomones in the Host-seeking Behaviour of the Malaria Mosquito Anopheles Gambiae Sensu Stricto (diptera: Culicidae)", Chem. Senses, vol. 30, 2005, pp. 145-152.
Stanczyk, et al., "Behavioral Insensitivity to DEET in Aedes Aegypti is a Genetically Determined Trait Residing in Changes in Sensillum Function", PNAS, vol. 107, No. 19, May 11, 2010, pp. 8575-8580.
Sweeney et al., "Targeted Expression of Tetanus Toxin Light Chain in Drosophila Specifically Eliminated Synaptic Transmission and Causes Behavioral Defects", Neuron, vol. 14, Feb. 1995, pp. 341-351.
Syed et al., "Acute Olfactory Response of Culex Mosquitoes to a Human—and Bird-derived Attractant", PNAS, vol. 106, No. 44, Nov. 3, 2009, pp. 18803-18808.
Syed et al., "Generic Insect Repellent Detector from the Fruit Fly *Drosophila Melanogaster*", Plos One, vol. 6, Issue 3, Mar. 2011, pp. 1-6.
Syed et al., "Maxillary Palps are Broad Spectrum Odorant Detectors in Culex Quinquefasciatus", Chem. Senses, vol. 32, 2007, pp. 727-738.
Tanaka et al., "Allyl derivatives as cockroach repellents", XP002744424, retrieved from STN Database Accession No. 1976:70350.
Turner et al., "Ultra-Prolonged Activation of $CO_2$ -Sensing Neurons Disorients Mosquitoes", Nature, vol. 474, No. 7349, 2011, pp. 87-91.
Verhulst et al., "Chemical Ecology of Interactions Between Human Skin Microbiota and Mosquitoes", FEMS Microbiol Ecol, vol. 74, 2010, pp. 1-9.
Verhulst et al., "Differential Attraction of Malaria Mosquitoes to Volatile Blends Produced by Human Skin Bacteria", Plos One, vol. 5, Issue 12, Dec. 2010, pp. 1-9.
Skinner et al., "Topical Mosquito Repellents IX: Quinolines, Isoquinolines, and Quinoxalines", Journal of Pharmaceutical Sciences, vol. 65, No. 9. Sep. 1976, pp. 1404-1407.
Walker et al., "Quantitative Structure—Activity Relationships for Predicting Percuataneous Absorption Rates", Environmental Toxicology and Chemistry, vol. 22, No. 8, 2003, pp. 1870-1884.
Wang et al., "Molecular Basis of Odor Coding in the Malaria Vector Mosquito Anopheles Gambiae", PNAS, vol. 107, No. 9, Mar. 2. 2010, pp. 4418-4423.
Wang et al., "QSAR Study of Mosquito Repellents from Terpenoid with a Six-Member-Ring", Bioorganic & Medicinal Chemistry Letters, vol. 18, No. 9, May 2008, pp. 2854-2859.
Weiss et al., "The Molecular and Cellular Basis of Bitter Taste in Drosophila", Neuron, vol. 69, No. 2 Jan. 2011, pp. 258-272.
Xia et al., "The Molecular and Cellular Basis of Olfactory-Driven Behavior in Anopheles Gambiae Larvae"PNAS, vol. 105, No. 17, Apr. 29, 2008, pp. 6433-6438.

(56) References Cited

OTHER PUBLICATIONS

Xue et al., "Field Evaluation of CDC and Mosquito Magneth X Traps Baited with Dry Ice, CO2 Sachet, and Octenol Against Mosquitoes", Journal of the American Mosquito Control Association, vol. 24, No. 2, 2008, pp. 249-252.

Lee et al., "Multiple Gustatory Receptors Required for the Caffeine Response in Drosophila", Proceedings of the National Academy of Sciences, vol. 106, No. 11, Mar. 17, 2009, pp. 4495-4500.

Zhu, Song-Nian, "Research on a Repellent for Ants and Rats for Plastics", Chemical Abstracts Service, Columbus, Ohio, US; 2004, XP002744300, Database accession No. 2004:1027260.

* cited by examiner

| Compound Name | Protection (Days) | Training Set 1 | Training Set 2 |
|---|---|---|---|
| N,N-diethyl-m-toluamine | 17.5 | Yes | Yes |
| 1-Acetyl-2-methylpiperidine | 2 | Yes | Yes |
| 1-(1-Oxopropyl)piperidine | 5 | Yes | Yes |
| 2-Ethyl-1-(1-oxopropyl)piperidine | 5 | Yes | Yes |
| 2-Methyl-1-(1-oxoheptyl)-piperidine | 17 | Yes | Yes |
| 3-Methyl-1-(1-oxoheptyl)piperidine | 15.5 | Yes | Yes |
| 4-Methyl-1-(1-oxooctyl)piperidine | 48 | Yes | Yes |
| 1-(1-Oxooctyl)-4-(phenylmethyl)piperidine | 13 | Yes | Yes |
| 2-Ethyl-1-(1-oxononyl)piperidine | 43 | Yes | Yes |
| 2-Methyl-1-(1-oxodecyl)piperidine | 49.5 | Yes | Yes |
| 4-Methyl-1-(1-oxodecyl)piperidine | 41 | Yes | Yes |
| 1-(1-Oxo-10-undecylenyl)piperidine | 50 | Yes | Yes |
| 2-Ethyl-1-(1-oxo-10-undecylenyl)piperidine | 53 | Yes | Yes |
| 1-(1-Oxo-10-undecylenyl)-4-(phenylmethyl)piperidine | 8.5 | Yes | Yes |
| 4-Methyl-1-(1-oxo-10-undecylenyl)piperidine | 73 | Yes | Yes |
| 1-(1-Oxoundecyl)piperidine | 39.5 | Yes | Yes |
| 2-Methyl-1-(1-oxododecyl)piperidine | 14.5 | Yes | Yes |
| 3-Methyl-1-(1-oxododecanyl)piperidine | 19.5 | Yes | Yes |
| 1-(1-Cyclohexen-1-ylcarbonyl)piperidine | 17 | Yes | Yes |
| 1-(Cyclohexylcarbonyl)piperidine | 14 | Yes | Yes |
| 1-(Cyclohexylcarbonyl)-2-ethylpiperidine | 17 | Yes | Yes |
| 1-(Cyclohexylcarbonyl)-3-methylpiperidine | 24.5 | Yes | Yes |
| 1-(Cyclohexylcarbonyl)-4-methylpiperidine | 35 | Yes | Yes |
| 1-(3-Cyclopentyl-1-oxopropyl)piperidine | 12 | Yes | Yes |
| 1-(1-Methylcyclohexylcarbonyl)-3-methylpiperidine | 33 | Yes | Yes |
| 2-Methyl-1-[(4-methylcyclohexyl)carbonyl]piperidine | 21.5 | Yes | Yes |
| 1-(Cyclohexylacetyl)-2-ethylpiperidine | 29.5 | Yes | Yes |
| 1-(Cyclohexylacetyl)-2-methylpiperidine | 47.5 | Yes | Yes |
| 1-(3-Cyclohexyl-1-oxopropyl)-2-methylpiperidine | 35 | Yes | Yes |
| 1-(3-Cyclohexyl-1-oxopropyl)-3-methylpiperidine | 45.5 | Yes | Yes |
| 1-(3-Cyclohexyl-1-oxopropyl)-4-methylpiperidine | | | |

| Compound Name | Protection (Days) | Training Set 1 | Training Set 2 |
|---|---|---|---|
| ethyl benzoate | 0 | Yes | Yes |
| ethyl butyrate | 0 | Yes | Yes |
| ethyl cinnamate | 0 | Yes | Yes |
| ethyl decanoate | 0 | Yes | Yes |
| ethyl hexanoate | 0 | Yes | Yes |
| ethyl lactate | 0 | Yes | Yes |
| ethyl methanoate | 0 | Yes | Yes |
| ethyl octanoate | 0 | Yes | Yes |
| ethyl propionate | 0 | Yes | Yes |
| ethyl trans-2-butenoate | 0 | Yes | Yes |
| ethyl-acetate | 0 | Yes | Yes |
| ethyl-butyrate | 0 | Yes | Yes |
| ethyl-formate | 0 | Yes | Yes |
| ethyl-hexanoate | 0 | Yes | Yes |
| ethyl-propanoate | 0 | Yes | Yes |
| eugenol | 0 | Yes | Yes |
| furfural | 0 | Yes | Yes |
| g-butyrolactone | 0 | Yes | Yes |
| g-decalactone | 0 | Yes | Yes |
| g-hexalactone | 0 | Yes | Yes |
| g-octalactone | 0 | Yes | Yes |
| gamma-decalactone | 0 | Yes | Yes |
| geranyl-acetone | 0 | Yes | Yes |
| glycerol | 0 | Yes | Yes |
| heptanal | 0 | Yes | Yes |
| heptane | 0 | Yes | Yes |
| heptanoic acid | 0 | Yes | Yes |
| hexadecanoic acid | 0 | Yes | Yes |
| hexanal | 0 | Yes | Yes |
| hexanoic acid | 0 | Yes | Yes |

*Figure 1*

| Compound Name | Protection (Days) | Training Set 1 | Training Set 2 | Compound Name | Protection (Days) | Training Set 1 | Training Set 2 |
|---|---|---|---|---|---|---|---|
| 4-cyclohexyl-1-(3-methylpiperidin-1-yl)butan-1-one | 33 | Yes | Yes | hexyl acetate | 0 | Yes | Yes |
| 1-(3-Cyclopentyl-1-oxopropyl)-2-ethylpiperidine | 40.5 | Yes | Yes | hexyl butyrate | 0 | Yes | Yes |
| 1-(3-Cyclohexyl-1-oxopropyl)-2-ethylpiperidine | 42 | Yes | Yes | hexyl hexanoate | 0 | Yes | Yes |
| 1-(Cyclohexylacetyl)-4-(phenylmethyl)piperidine | 3 | Yes | Yes | indole | 0 | Yes | Yes |
| 1-(3-Cyclohexyl-1-oxopropyl)-4-(phenylmethyl)piperidine | 12 | Yes | Yes | isoamyl-acetate | 0 | Yes | Yes |
| (Z)2-hexenol | 0 | Yes | Yes | isobutyl acetate | 0 | Yes | Yes |
| 1-butanol | 0 | Yes | Yes | isobutyric acid | 0 | Yes | Yes |
| 1-chlorododecane | 0 | Yes | Yes | isopentanoic acid | 0 | Yes | Yes |
| 1-dodecanol | 0 | Yes | Yes | isopentyl acetate | 0 | Yes | Yes |
| 1-hepten-3-ol | 0 | Yes | Yes | isovaleric acid | 0 | Yes | Yes |
| 1-hexanol | 0 | Yes | Yes | L(+)-lactic acid | 0 | Yes | Yes |
| 1-hexen-3-ol | 0 | Yes | Yes | lactic acid | 0 | Yes | Yes |
| 1-octanol | 0 | Yes | Yes | linoleic acid | 0 | Yes | Yes |
| 1-octen-3-ol | 0 | Yes | Yes | methanoic acid | 0 | Yes | Yes |
| 1-pentanol | 0 | Yes | Yes | methanol | 0 | Yes | Yes |
| 1-penten-3-ol | 0 | Yes | Yes | methyl acetate | 0 | Yes | Yes |
| 1-propanol | 0 | Yes | Yes | methyl benzoate | 0 | Yes | Yes |
| 2-acetylpyridine | 0 | Yes | Yes | methyl butyrate | 0 | Yes | Yes |
| 2-acetylthiazole | 0 | Yes | Yes | methyl hexanoate | 0 | Yes | Yes |
| 2-acetylthiophene | 0 | Yes | Yes | methyl octanoate | 0 | Yes | Yes |
| 2-butanone | 0 | Yes | Yes | methyl salicylate | 0 | Yes | Yes |
| 2-ethoxythiazole | 0 | Yes | Yes | methyl-2-methyl benzoate | 0 | Yes | Yes |
| 2-ethyl toluene | 0 | Yes | Yes | methyl-octanoate | 0 | Yes | Yes |
| 2-ethyl-1-hexanol | 0 | Yes | Yes | methyl-propanoate | 0 | Yes | Yes |
| 2-ethylhexanoic acid | 0 | Yes | Yes | nonanal | 0 | Yes | Yes |
| 2-ethylphenol | 0 | Yes | Yes | nonanoic acid | 0 | Yes | Yes |
| 2-heptanone | 0 | Yes | Yes | octadecanoic acid | 0 | Yes | Yes |
| 2-iso-butyl thiazole | 0 | Yes | Yes | octanal | 0 | Yes | Yes |
| 2-methylphenol | 0 | Yes | Yes | octanoic acid | 0 | Yes | Yes |
| 2-nonanone | 0 | Yes | Yes | pentanal | 0 | Yes | Yes |

*Figure 1 (Continued)*

| Compound Name | Protection (Days) | Training Set 1 | Training Set 2 | Compound Name | Protection (Days) | Training Set 1 | Training Set 2 |
| --- | --- | --- | --- | --- | --- | --- | --- |
| 2-oxobutanoic acid | 0 | Yes | Yes | pentanoic acid | 0 | Yes | Yes |
| 2-oxohexenoic acid | 0 | Yes | Yes | pentyl acetate | 0 | Yes | Yes |
| 2-oxopentanoic acid | 0 | Yes | Yes | phenethyl acetate | 0 | Yes | Yes |
| 2-oxopropanoic acid | 0 | Yes | Yes | phenethyl alcohol | 0 | Yes | Yes |
| 2-pentanol | 0 | Yes | Yes | phenol | 0 | Yes | Yes |
| 2-pentanone | 0 | Yes | Yes | phenylacetaldehyde | 0 | Yes | Yes |
| 2-phenoxy ethanol | 0 | Yes | Yes | propanal | 0 | Yes | Yes |
| 2-propenal | 0 | Yes | Yes | propionic acid | 0 | Yes | Yes |
| 2-propylphenol | 0 | Yes | Yes | propyl acetate | 0 | Yes | Yes |
| 2,3-butanediol | 0 | Yes | Yes | putrescine | 0 | Yes | Yes |
| 2,3-butanedione | 0 | Yes | Yes | pyruvic acid | 0 | Yes | Yes |
| 3-methyl-1-butanol | 0 | Yes | Yes | tetradecanoic acid | 0 | Yes | Yes |
| 3-methyl-2-buten-1-ol | 0 | Yes | Yes | thiazole | 0 | Yes | Yes |
| 3-methyl-2-cyclohexenol | 0 | Yes | Yes | tridecanoic acid | 0 | Yes | Yes |
| 3-methyl-2-hexenoic acid | 0 | Yes | Yes | Z2-hexenol | 0 | Yes | Yes |
| 3-methylbutanol | 0 | Yes | Yes | Z3-hexenol | 0 | Yes | Yes |
| 3-methylindole | 0 | Yes | Yes | Picaridin | 17.5 | Yes | Yes |
| 3-methylphenol | 0 | Yes | Yes | Linalool | 17.5 | Yes | Yes |
| 3-methylthio-1-propanol | 0 | Yes | Yes | aplha-Thujone | 17.5 | Yes | Yes |
| 3-octanone | 0 | Yes | Yes | beta-Thujone | 17.5 | Yes | Yes |
| 4-ethyl guaiacol | 0 | Yes | Yes | Eucalyptol | 17.5 | Yes | Yes |
| 4-ethylphenol | 0 | Yes | Yes | N-butyl-N-methyl-hexanamide | 3.645 | No | Yes |
| 4-methylcyclohexanol | 0 | Yes | Yes | N-butyl-N-ethylhexanamide | 4.86 | No | Yes |
| 4-methylphenol | 0 | Yes | Yes | N,N-diallylhexanamide | 2.43 | No | Yes |
| 4-methylthiazole | 0 | Yes | Yes | Hexahydro-1-(1-oxohexyl)-1H-a | 17.01 | No | Yes |
| 4,5-dimethylthiazole | 0 | Yes | Yes | N-cyclohexyl-N-ethylhexanamid | 29.16 | No | Yes |
| 5-alpha-androst-16-one | 0 | Yes | Yes | N-ethyl-N-phenylhexanamide | 18.225 | No | Yes |
| 5-alpha-androsten-3-alpha-ol | 0 | Yes | Yes | N-butyl-N-ethyl-2-methylpentan | 2.43 | No | Yes |
| 6-methyl-5-hepten-2-one | 0 | Yes | Yes | 1-(1-azepanyl)-2-methyl-1-pent | 8.505 | No | Yes |
| 7-octenoic acid | 0 | Yes | Yes | N-butyl-N,2-diethylbutanamide | 7.29 | No | Yes |

*Figure 1 (Continued)*

| Compound Name | Protection (Days) | Training Set 1 | Training Set 2 | Compound Name | Protection (Days) | Training Set 1 | Training Set 2 |
|---|---|---|---|---|---|---|---|
| acetaldehyde | 0 | Yes | Yes | N,2-diethyl-N-(2-methyl-2-prop | 2.43 | No | Yes |
| acetic acid | 0 | Yes | Yes | N-butyl-N-ethyl-3-methylbutana | 2.43 | No | Yes |
| acetone | 0 | Yes | Yes | N,N-diisobutyl-3-methylbutanan | 2.43 | No | Yes |
| acetophenone | 0 | Yes | Yes | N-cyclohexyl-N-ethyl-3-methylb | 17.01 | No | Yes |
| amyl-acetate | 0 | Yes | Yes | N-butyl-N-ethyl-2,2-dimethylpro | 2.43 | No | Yes |
| benzaldehyde | 0 | Yes | Yes | N-ethyl-2,2-dimethyl-N-(2-meth | 2.43 | No | Yes |
| benzyl acetate | 0 | Yes | Yes | 1-(1-azepanyl)-2,2-dimethyl-1-g | 2.43 | No | Yes |
| benzyl alcohol | 0 | Yes | Yes | N-butyl-N-ethyl-2-methylbenzar | 36.45 | No | Yes |
| butanal | 0 | Yes | Yes | (E)-N-butyl-N-ethyl-2-methyl-2- | 4.86 | No | Yes |
| butanoic acid | 0 | Yes | Yes | (E)-N-ethyl-2-methyl-N-(2-meth | 4.86 | No | Yes |
| butyl acetate | 0 | Yes | Yes | (E)-1-(1-azepanyl)-2-methyl-2- | 9.72 | No | Yes |
| butyric acid | 0 | Yes | Yes | (E)-2-methyl-N,N-di-2-propenyl | 4.86 | No | Yes |
| cadaverine | 0 | Yes | Yes | N-ethyl-2-methyl-N-(2-methyl-2 | 31.59 | No | Yes |
| cis-9-octadecenoic acid | 0 | Yes | Yes | N-ethyl-2-methyl-N-phenyl-ben | 8.505 | No | Yes |
| cyclohexanone | 0 | Yes | Yes | N-butyl-N-ethyl-3-methyl-2-but | 2.43 | No | Yes |
| d-decalactone | 0 | Yes | Yes | N-ethyl-3-methyl-N-(2-methyl-2 | 2.43 | No | Yes |
| decanal | 0 | Yes | Yes | N,N-diisobutyl-3-methyl-crotona | 4.86 | No | Yes |
| decanoic acid | 0 | Yes | Yes | Hexahydro-1-(3-methylcrotonoy | 7.29 | No | Yes |
| delta-decalactone | 0 | Yes | Yes | N-butyl-N-ethyl-cinnamamide | 20.655 | No | Yes |
| diethyl succinate | 0 | Yes | Yes | N,N-bis(2-methylpropyl)-3-phen | 4.86 | No | Yes |
| dimethyl sulfide | 0 | Yes | Yes | N-ethyl-N,3-diphenyl-2-propena | 2.43 | No | Yes |
| dimethylsulfide | 0 | Yes | Yes | (E)-N-n-butyl-N-ethyl-2-hexena | 18.225 | No | Yes |
| dodecanoic acid | 0 | Yes | Yes | (E)-N,N-di-(2-methylpropyl)-2- | 19.44 | No | Yes |
| E2-hexenal | 0 | Yes | Yes | (E)-N-cyclohexyl-N-ethyl-2-hexe | 53.46 | No | Yes |
| E2-hexenol | 0 | Yes | Yes | N-butyl-N-methyl-5-hexynamide | 17.01 | No | Yes |
| E2-hexenyl acetate | 0 | Yes | Yes | N,3-dicyclohexyl-N-ethylpropana | 0 | No | Yes |
| E3-hexenol | 0 | Yes | Yes | (E)-N,2-dimethyl-N-octylpent-2- | 0 | No | Yes |
| ethanol | 0 | Yes | Yes | N-cyclohexyl-N-methylheptanam | 0 | No | Yes |
| ethyl 3-hydroxybutyrate | 0 | Yes | Yes | (E)-N-cyclohexyl-N-ethyl-2-met | 0 | No | Yes |

*Figure 1 (Continued)*

| symbol | brief description | class | dimensionality | occurrence |
|---|---|---|---|---|
| B05[C-N] | presence/absence of C - N at topological distance 05 | 2D binary fingerprints | 2 | 3 |
| EEig15r | Eigenvalue 15 from edge adj. matrix weighted by resonance integrals | edge adjacency indices | 2 | 2 |
| B06[C-N] | presence/absence of C - N at topological distance 06 | 2D binary fingerprints | 2 | 3 |
| Mor07p | 3D-MoRSE - signal 07 / weighted by atomic polarizabilities | 3D-MoRSE descriptors | 3 | 1 |
| GVWAI-80 | Ghose-Viswanadhan-Wendoloski drug-like index at 80% | molecular properties | 0 | 1 |
| N-072 | RCO-N< / >N-X=X | atom-centered fragments | 1 | 9 |
| EEig12d | Eigenvalue 12 from edge adj. matrix weighted by dipole moments | edge adjacency indices | 2 | 1 |
| RDF055u | Radial Distribution Function - 5.5 / unweighted | RDF descriptors | 3 | 1 |
| Mor32v | 3D-MoRSE - signal 32 / weighted by atomic van der Waals volumes | 3D-MoRSE descriptors | 3 | 1 |
| BELc6 | lowest eigenvalue n. 6 of Burden matrix / weighted by atomic Sanderson electronegativities | Burden eigenvalues | 3 | 2 |
| O-060 | Al-O-Ar / Ar-O-Ar / R..O..R / R-O-C=X | atom-centered fragments | 1 | 2 |
| J3D | 3D-Balaban index | geometrical descriptors | 3 | 2 |
| RDF050u | Radial Distribution Function - 5.0 / unweighted | RDF descriptors | 3 | 1 |
| EEig13r | Eigenvalue 13 from edge adj. matrix weighted by resonance integrals | edge adjacency indices | 2 | 1 |
| F03[C-N] | frequency of C - N at topological distance 03 | 2D frequency fingerprints | 2 | 1 |
| H6m | H autocorrelation of lag 6 / weighted by atomic masses | GETAWAY descriptors | 3 | 1 |
| DISPm | d COMMA2 value / weighted by atomic masses | geometrical descriptors | 3 | 1 |
| RDF055p | Radial Distribution Function - 5.5 / weighted by atomic polarizabilities | RDF descriptors | 3 | 1 |
| Infective-80 | Ghose-Viswanadhan-Wendoloski anti-infective-like index at 80% | molecular properties | 0 | 1 |
| Ui | unsaturation index | molecular properties | 0 | 1 |
| SRW06 | self-returning walk count of order 06 | walk and path counts | 2 | 1 |
| PCD | difference between multiple path count and path count | walk and path counts | 2 | 1 |
| EEig08x | Eigenvalue 08 from edge adj. matrix weighted by edge degrees | edge adjacency indices | 2 | 1 |
| RDF040p | Radial Distribution Function - 4.0 / weighted by atomic polarizabilities | RDF descriptors | 3 | 1 |
| B02[O-O] | presence/absence of O - O at topological distance 02 | 2D binary fingerprints | 2 | 1 |
| De | D total accessibility index / weighted by atomic Sanderson electronegativities | WHIM descriptors | 3 | 1 |
| R8e+ | R maximal autocorrelation of lag 8 / weighted by atomic Sanderson electronegativities | GETAWAY descriptors | 3 | 1 |
| IC1 | information content index (neighborhood symmetry of 1-order) | information indices | 2 | 1 |
| F02[N-O] | frequency of N - O at topological distance 02 | 2D frequency fingerprints | 2 | 1 |
| nRCONR2 | number of tertiary amides (aliphatic) | functional group counts | 1 | 1 |
| H-047 | H attached to C1(sp3)/C0(sp2) | atom-centered fragments | 1 | 1 |

FIGURE 10

| symbol | brief description | class | dimensionality | occurrence |
|---|---|---|---|---|
| B05[C-N] | presence/absence of C - N at topological distance 05 | 2D binary fingerprints | 2 | 2 |
| EEig15r | Eigenvalue 15 from edge adj. matrix weighted by resonance integrals | edge adjacency indices | 2 | 1 |
| RDF055e | Radial Distribution Function - 5.5 / weighted by atomic Sanderson electronegativities | RDF descriptors | 3 | 1 |
| piPC10 | molecular multiple path count of order 10 | walk and path counts | 2 | 1 |
| F03[C-N] | frequency of C - N at topological distance 03 | 2D frequency fingerprints | 2 | 2 |
| J3D | 3D-Balaban index | geometrical descriptors | 3 | 3 |
| N-072 | RCO-N< / >N-X=X | atom-centered fragments | 1 | 1 |
| EEig15x | Eigenvalue 15 from edge adj. matrix weighted by edge degrees | edge adjacency indices | 2 | 1 |
| B06[C-N] | presence/absence of C - N at topological distance 06 | 2D binary fingerprints | 2 | 2 |
| Mor27u | 3D-MoRSE - signal 27 / unweighted | 3D-MoRSE descriptors | 3 | 1 |
| RDF040p | Radial Distribution Function - 4.0 / weighted by atomic polarizabilities | RDF descriptors | 3 | 1 |
| RDF055m | Radial Distribution Function - 5.5 / weighted by atomic masses | RDF descriptors | 3 | 2 |
| EEig12d | Eigenvalue 12 from edge adj. matrix weighted by dipole moments | edge adjacency indices | 2 | 1 |
| EEig15d | Eigenvalue 15 from edge adj. matrix weighted by dipole moments | edge adjacency indices | 2 | 3 |
| Mor25e | 3D-MoRSE - signal 25 / weighted by atomic Sanderson electronegativities | 3D-MoRSE descriptors | 3 | 1 |
| Mor32m | 3D-MoRSE - signal 32 / weighted by atomic masses | 3D-MoRSE descriptors | 3 | 1 |
| B02[O-O] | presence/absence of O - O at topological distance 02 | 2D binary fingerprints | 2 | 1 |
| ZM2V | second Zagreb index by valence vertex degrees | topological descriptors | 2 | 1 |
| BELe6 | lowest eigenvalue n. 6 of Burden matrix / weighted by atomic Sanderson electronegativities | Burden eigenvalues | 3 | 1 |
| EEig13x | Eigenvalue 13 from edge adj. matrix weighted by edge degrees | edge adjacency indices | 2 | 1 |
| nRCOOR | number of esters (aliphatic) | functional group counts | 1 | 1 |
| H8v | H autocorrelation of lag 8 / weighted by atomic van der Waals volumes | GETAWAY descriptors | 3 | 1 |
| C-005 | CH3X | atom-centered fragments | 2 | 1 |
| DISPv | d COMMA2 value / weighted by atomic van der Waals volumes | geometrical descriptors | 3 | 1 |
| Infective-80 | Ghose-Viswanadhan-Wendoloski anti-infective-like index at 80% | molecular properties | 0 | 1 |
| H-047 | H attached to C1(sp3)/C0(sp2) | atom-centred fragments | 1 | 1 |
| EEig08x | Eigenvalue 08 from edge adj. matrix weighted by edge degrees | edge adjacency indices | 2 | 1 |
| Mor32v | 3D-MoRSE - signal 32 / weighted by atomic van der Waals volumes | 3D-MoRSE descriptors | 3 | 1 |
| H-046 | H attached to C0(sp3) no X attached to next C | atom-centred fragments | 1 | 3 |
| B09[C-Cl] | presence/absence of C - Cl at topological distance 09 | 2D binary fingerprints | 2 | 1 |
| EEig09d | Eigenvalue 09 from edge adj. matrix weighted by dipole moments | edge adjacency indices | 2 | 1 |

FIGURE 11

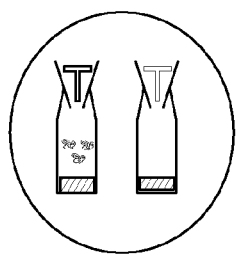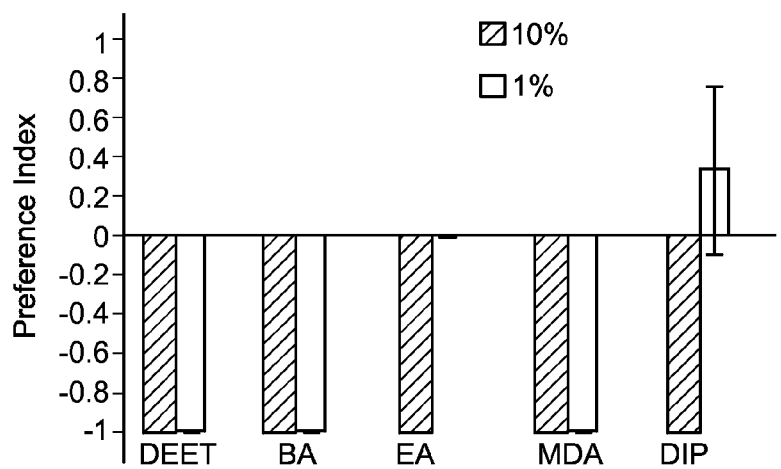
Figure 13

METHODS FOR ASSESSING REPELLANT QUALITY OF ORGANIC MATERIALS AND METHODS AND COMPOSITIONS FOR REPELLING ARTHROPODS

CROSS REFERENCE TO RELATED APPLICATION

This is a U.S. National Phase Patent Application of PCT/US2012/060673, filed Oct. 17, 2012, which claims the benefit under 35 U.S.C. §119(e) of U.S. Provisional Application Ser. No. 61/548,141 filed Oct. 17, 2011, the disclosure of which is hereby incorporated by reference in its entirety.

TECHNICAL FIELD

The disclosure provides compounds useful as insect repellents and compositions comprising such repellents. The disclosure further provides compounds useful as insect attractants and compositions comprising such attractants. The disclosure further provides compounds useful as insect traps.

BACKGROUND

Numerous insects are vectors for disease. Mosquitoes in the genus *Anopheles* are the principle vectors of malaria, a disease caused by protozoa in the genus *Trypanosoma*. *Aedes aegypti* is the main vector of the viruses that cause Yellow fever and Dengue. Other viruses, the causal agents of various types of encephalitis, are also carried by *Aedes* spp. mosquitoes. *Wuchereria bancrofti* and *Brugia malayi*, parasitic roundworms that cause filariasis, are usually spread by mosquitoes in the genera *Culex, Mansonia,* and *Anopheles*.

Horse flies and deer flies may transmit the bacterial pathogens of tularemia (*Pasteurella tularensis*) and anthrax (*Bacillus anthracis*), as well as a parasitic roundworm (*Loa boa*) that causes loiasis in tropical Africa.

Eye gnats in the genus *Hippelates* can carry the spirochaete pathogen that causes yaws (*Treponema pertenue*), and may also spread conjunctivitis (pinkeye). Tsetse flies in the genus *Glossina* transmit the protozoan pathogens that cause African sleeping sickness (*Trypanosoma gambiense* and *T. rhodesiense*). Sand flies in the genus *Phlebotomus* are vectors of a bacterium (*Bartonella bacilliformis*) that causes Carrion's disease (oroyo fever) in South America. In parts of Asia and North Africa, they spread a viral agent that causes sand fly fever (pappataci fever) as well as protozoan pathogens (*Leishmania* spp.) that cause Leishmaniasis.

Most blood feeding insects, including mosquitoes, sandflies, Testse flies, use olfactory cues to identify human hosts. This group of hematophagous insects can transmit a wide assortment of deadly human diseases that together cause more suffering and deaths globally than any other disease condition. Diseases transmitted by such insects include malaria, dengue fever, yellow fever, West Nile virus, filariasis, river blindness, epidemic polyarthritis, Leshmaniasis, trypanosomiasis, Japanese encephalitis, St. Louis Encephalitis amongst others.

The olfactory system can detect and discriminate amongst an extremely large number of volatile compounds in the environment, and this is critical for important behaviors like finding hosts, finding food, finding mates, and avoiding predators. To detect this wide variety of volatiles, most organisms have evolved extremely large families of receptor genes that typically encode 7-transmembrane proteins expressed in the olfactory neurons. Little is known, however, about what structural characteristics of small volatile molecules are important for behavior modification. The predicted odors provided herein are able to manipulate the olfactory-based behavior of an organism by making use of computationally identified important structural characteristics.

Volatile chemical space is immense. Odors in the environment that have been catalogued in some plant sources alone number more than a couple thousand. A very small proportion of chemical space has been systematically tested for the ability to modify behavior, and a very small fraction of odor receptors, whose sequences are known, have been tested for their ability to be affected by behavior modifying odors. The complete 3-D structures of odor receptor proteins have not yet been determined, thus modeling of odor-protein interactions is not yet possible except in rare instances. Furthermore, were a 3-D receptor structure to become available, application of one odor-receptor interaction to study others may be confounded by the possibility of multiple ligand binding sites in a single receptor, as well as the sequence divergence amongst different odor receptors. The disclosure was identified by intelligent and rapid screening of untested volatile chemical space through computational identification of important characteristics shared between known behavior modifying compounds, circumventing many of the previously described obstacles. Additionally, one can screen potential odors for toxicological safety. The disclosure has been used to identify molecular features important in mosquito avoidance. The identified features were then used to screen a vast chemical space, predicting odors that interrupt host-seeking behavior.

Several repellent compounds have been identified to date. These compounds range from naturally occurring extracts to commercially manufactured compounds. The degree of protection, duration of protection, and safety of these odors varies greatly. The gold standard of these compounds generally considered DEET.

DEET (N,N-diethyl-3-methylbenzamide) has been used for insect repellency for over 50 years. Protection is generally provided by direct application to the skin in concentrations ranging from 3 to 100 percent (Household products database of NLM). While results vary across experiments, DEET has been shown to act as an irritant and in some cases may cause skin reactions. In a recent study DEET has also just recently been shown to inhibit acetylcholoinesterase in humans, which is an important neurotransmitter. DEET is also known to dissolve several products including certain plastics, synthetic fabrics, painted or varnished surfaces. How DEET is detected by arthropods is currently unknown. Several candidate methods have been proposed, but sufficient evidence that any of these methods is the direct avoidance-inducing pathway has not been demonstrated. As an example, it has been demonstrated that *Culex quinquefasciatus* are able to directly detect DEET through a short trichoid sensillum in a dose dependent manner. It has also been proposed that *Drosophila* are able to detect DEEN through gustatory receptors. It is possible that mosquitoes recognize this compound through a combination of olfactory and gustatory pathways.

Several other terpenoid compounds with repellent properties including thujone, eucalyptol, and linalool have also been identified. These compounds were shown to directly activate a trichoid sensillum housed odor receptor, which is also activated by DEET, only more strongly than DEET itself.

Icaridin, which is also called picaridine, is also used as an insect repellent. Similarly to DEET it acts as a repellent to several different insect species. Icaridin has the added benefit of not melting plastics. It has been found to be as effective as DEET at repelling insects, while being less irritating than DEET.

In two recent studies, 34 N-acylpiperdine and 38 carboxamide mosquito repellent candidates were synthesized and compared for their effectiveness. 19 of the N-acylpiperdine and 7 of the carboxamide compounds were either as effective as or more effective than DEET at repelling *Aedes aegypti* at a concentration of 25 $\mu$mol/cm$^2$ using a protection time assay. The mode of repellency for all of these compounds is unknown. As the N-acylpiperdines and some of the carboxamides are larger and likely have a lower vapor pressure than DEET, it is possible that the increased protection times of these compounds is due to a slower evaporation rate.

Traditional vector control methods often involve the heavy use of chemical insecticides that are harmful to the environment and often to human health. Moreover, insects can develop resistance to these chemicals, suggesting that there is a need to identify novel ways of insect control that are effective, cheap, and environmentally friendly. Integrating methods that inhibit vector-human contact, such as vector control and the use of insect repellents, bednets, or traps, may play a complementary and critical role in controlling the spread of these deadly diseases.

In insects host-odor cues, among others, are detected by olfactory receptor neurons (ORNs) that are present on the surface of at least two types of olfactory organs, the antennae and the maxillary palps. The antenna is the main olfactory organ and its surface is covered by hundreds of sensilla, each of which is innervated by the dendrites of 1-5 ORNs. Odor molecules pass through pores on the surface of sensilla and activate odor receptor proteins present on the dendritic membranes of the ORNs.

The odor receptor (Or) gene family in insects was first identified in *D. melanogaster*. It includes a highly divergent family of 60 Odor receptor (Or) genes that encode proteins predicted to contain seven trans-membrane regions.

Odor responses of ORNs on the surface of the antennae and maxillary palps have been studied using two separate techniques. Whole organ recordings called electroantennograms (EAGs) and electropalpograms (EPGs) have been used to detect the aggregate electrical activities from a large number of neurons in response to odors. A more sensitive and exact method has also been used to examine the functional properties of olfactory neurons within a single sensillum, and neurons that respond to behaviourally important ligands such as $CO_2$, ammonia, phenols, 1-octen-3-ol, lactic acid, and carboxylic acids have been identified.

Odor receptor responses to odorants have been tested in vivo in the organism of interest predominately through two separate techniques. One approach involves whole organ recordings called electroantennograms (EAGs), eletropalpograms (EPGs), and electroolfactograms (EOGs) which have been used to detect the aggregate electrical activities from a large number of olfactory neurons in response to odors. This technique does not allow for differentiation between odor receptor neuron responses and thus does not allow for identification of individual odor receptor responses to an odorant. A more sensitive and precise technique called single unit electrophysiology allows for individual odor receptor neuron responses to odors to be quantitatively measured. This technique either requires the odor receptor map to have been previously established by molecular tools or use of an "empty-neuron" system that utilizes a transgenic approach.

Additionally, other in vivo techniques have been used involving testing individual odor receptors of interest through transgenic expression in other organisms. Heterologous expression of Odor receptor genes from many species has been performed in Xenopus oocytes and Human Embryonic Kidney (HEK) 293 cells. Exposure of these cells to volatile compounds allows for a quantitative measure of response.

While these systems do provide a means to specifically express an odor receptor and obtain a quantitative measure of activation to a panel of odorants, their use is a very time consuming, expensive, and difficult process. Use of the "empty neuron" system and other heterologous expression approaches require transgenic fly lines to be produced or cDNA expression constructs made for each odor receptor to be tested. It has also been debated whether these expression systems produce wild type responses in all cases, as some cell specific components such as odorant binding proteins (OBPs) may be absent. Additionally all systems require the requirement of purchasing odors, diluting them, and performing the technically challenging testing of odorants.

In previous studies, individual odor receptors have sometimes been found to recognize compounds of similar functional groups containing similar hydrocarbon chain lengths. In addition it has also been shown that many Ors can be responsive to multiple distinct groups of structurally similar compounds. This property of odor receptors recognizing structurally similar compounds provides a framework for using cheminformatic similarity measures to predict novel active odorants.

Molecular descriptors are able to describe the structure of molecules through computationally derived values, which represent zero, one, two, or three-dimensional information of a compound. These descriptor type dimensionalities confer molecular information through classes such as constitutional, structural fragment, topographic, or spatial information, respectively.

Comparison of molecular descriptors to identify commonalities between highly active odorant structures has recently proven to be highly beneficial. In species where a specific behaviour, such as avoidance, has been tested against a panel of odors it is possible to use molecular descriptors to identify novel potential ligands using the known actives as a training set. For instance, the structure of N,N-diethyl-m-toluamide (DEET) was recently used to create a focused structural library, which was computationally ranked using Artificial Neural Networks (ANNs), and used to identify a more potent mosquito repellent. In another study a group analyzed *Drosophila* ORN responses to odors to identify activation metrics that were used to predict and test ligands from a small set of 21 compounds (Schmuker et al., 2007). The success rate of this strategy, as established by applying a neuronal firing rate cut-off of 50 spikes/sec to categorize activators, was <25%. Most recently a multi species approach was used to identify molecular descriptors that were important in compounds involved in olfaction however predictions were not possible. In another study by the same lab, an electronic nose was trained such that when presented with a novel odor it could predict whether or not the odor would activate an individual Or.

Therefore, there remains a need for computational methods that identify molecular descriptors that are useful in identifying arthropod repellants and/or attractants.

SUMMARY

The disclosure provides methods to assess the biological response of insect repellents. Molecular structural properties were identified that are shared between odors known to cause avoidance behavior in mosquitoes. By identifying the molecular features shared by the repellents, an in silico screen was performed of a large chemical space (hundreds of thousands of possible odors) to rapidly classify compounds for further biological effects assessment based on cost, efficacy and safety.

The details of one or more embodiments of the disclosure are set forth in the accompanying drawings and the description below. Other features, objects, and advantages of the disclosure will be apparent from the description and drawings, and from the claims.

The disclosure provides for a method of repelling an arthropod, including exposing the arthropod with a repelling composition, wherein the repelling compositions includes one or more compounds selected from the group consisting of methyl N,N-dimethyl anthranilate, ethyl anthranilate, butyl anthranilate, or 2,3-dimethyl-5-isobutyl pyrizine. In some embodiments, the repelling composition further includes one or more compounds from Table 1, below. In other embodiments, the repelling composition further includes one or more compounds from Table 2, below. In some embodiments, the repelling composition is applied on the body of one or more vertebrates or one or more plants to expose the repelling composition to the arthropod. In some embodiments, the repelling composition is formulated as a lotion, cream, dust, cosmetic, perfume, spray, paste, slow-release granule, paint, treated clothing, treated netting, treated building material, or incense. In some embodiments, the exposing the arthropod with the repelling composition is carried out using a vaporizer, evaporator, fan, heat, candle, or wicked apparatus. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

The disclosure further provides for a method of repelling an arthropod including exposing the arthropod with a repelling composition, wherein the repelling composition includes one or more compounds listed in Table 2. In some embodiments, the repelling composition includes two or more compounds listed in Table 2. In some embodiments, the repelling composition is applied on the body of one or more vertebrates or one or more plants to expose the repelling composition to the arthropod. In some embodiments, the repelling composition is formulated as a lotion, cream, dust, cosmetic, perfume, spray, paste, slow-release granule, paint, treated clothing, treated netting, treated building material, or incense. In some embodiments, the exposing the arthropod with the repelling composition is carried out using a vaporizer, evaporator, fan, heat, candle, or wicked apparatus. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

The disclosure further provides for a method of repelling an arthropod including exposing the arthropod with a repelling composition, wherein the repelling composition includes one or more compounds listed in Table 1. In some embodiments, the repelling composition includes two or more compounds listed in Table 1. In other embodiments, the repelling composition further includes one or more compounds listed in Table 2. In some embodiments, the repelling composition is applied on the body of one or more vertebrates or one or more plants to expose the repelling composition to the arthropod. In some embodiments, the repelling composition is formulated as a lotion, cream, dust, cosmetic, perfume, spray, paste, slow-release granule, paint, treated clothing, treated netting, treated building material, or incense. In some embodiments, the exposing the arthropod with the repelling composition is carried out using a vaporizer, evaporator, fan, heat, candle, or wicked apparatus. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

The disclosure further provides a method of repelling an arthropod including exposing the arthropod with a repelling composition, wherein the repelling composition includes a compound of formula I:

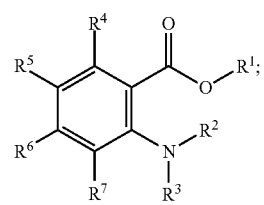

(I)

wherein:

$R^1$ is selected from the group consisting of H, C1-C12 alkyl, C2-C12 alkenyl, aryl, arylalkyl, cycloalkyl, cycloalkylalkyl, cycloalkenyl, and cycloakenylalkyl;

$R^2$ and $R^3$ are each independently selected from the group consisting of H, C1-C12 alkyl, benzoyl, cycloalkyl, cycloalkylalkyl, cycloakenyl, cycloakenylalkyl, arylalkyl, formyl, acyl, and $R^2$ and $R^3$ taken together form an =C—$R^8$;

$R^4$, $R^5$, $R^6$, and $R^7$ are each independently selected from the group consisting of H, C1-C4 alkyl, halo, and alkoxy; and $R^8$ is C1-C12 akyl, C2-C12 alkenyl, aryl, arylalkyl, cycloalkyl, cycloalkylalkyl, cycloakenyl, and cycloakenylalkyl. In some embodiments, $R^1$ is C1-C4 alkyl. In some embodiments, $R^1$ is $CH_3$, $CH_2CH_3$, or $CH_2CH_2CH_2CH_3$. In some embodiments, $R^1$ is $CH_3$, $CH_2CH_3$, or $CH_2CH_2CH_2CH_3$ and $R^2$ and $R^3$ is H. In some embodiments, the compound of formula I is methyl N,N-dimethyl anthranilate, ethyl anthranilate, or butyl anthranilate. In some embodiments, the repelling composition is applied on the body of one or more vertebrates or one or more plants to expose the repelling composition to the arthropod. In some embodiments, the repelling composition is formulated as a lotion, cream, dust, cosmetic, perfume, spray, paste, slow-release granule, paint, treated clothing, treated netting, treated building material, or incense. In some embodiments, the exposing the arthropod with the repelling composition is carried out using a vaporizer, evaporator, fan, heat, candle, or wicked apparatus. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

The disclosure further provides an arthropod repelling composition including two or more compounds listed in Table 1; two or more compounds listed in the Table 2; or two or more compounds selected from the group consisting of methyl N,N-dimethyl anthranilate, ethyl anthranilate, butyl anthranilate, or 2,3-dimethyl-5-isobutyl pyrizine. In some embodiments, the repelling composition is formulated as a lotion, cream, dust, cosmetic, perfume, spray, paste, slow-release granule, paint, treated clothing, treated netting, treated building material, or incense. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

DESCRIPTION OF DRAWINGS

FIG. 1 is a list of odors used in training set for repellency predictions.

FIG. 10 shows the optimized descriptor set calculated for training set 1.

FIG. 11 shows the optimized descriptor set calculated for training set 2.

FIG. 13 shows the Preference Index of *Drosophila melanogaster* adults to predicted repellents at two different concentrations in a two choice trap assay measured after 24 hrs. N=3-10 trials each treatment (trials with <30% participation were excluded), 10 flies/trial, error bars=s.e.m. (DEET=N,N-diethyl-3-methylbenzamide; BA=butyl anthranilate; EA=ethyl anthranilate; MDA=methyl N,N-dimethyl anthranilate; DIP=2,3-dimethyl-5-isobutyl pyrizine; Preference Index=number of flies in treated trap/(number of flies in treated+control traps).

DETAILED DESCRIPTION

Figure 2:
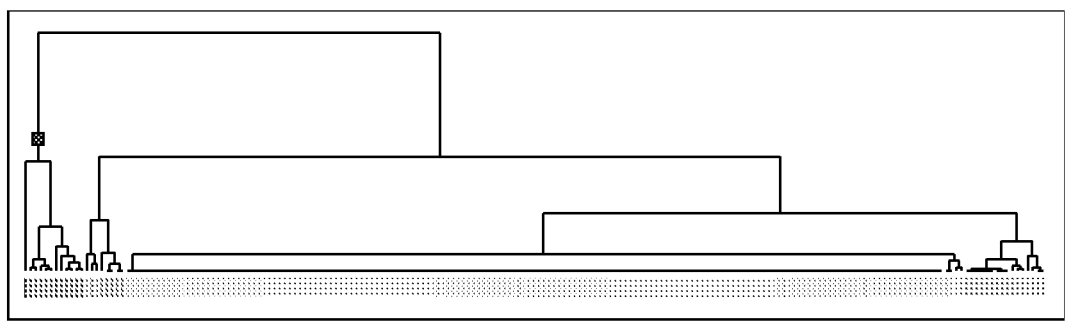
FIG. 2 depicts compound repellency classification through repellency clustering using a first training set.

The methods of the disclosure allows intelligent and rapid screening of untested volatile chemical space by computationally identifying important characteristics shared between known active compounds. Also provided are compounds identified by the methods of the disclosure for use as insect repellents and attractants.

1. Definitions

As used herein and in the appended claims, the singular forms "a," "and," and "the" include plural referents unless the context clearly dictates otherwise. Thus, for example, reference to "an insect" includes a plurality of such insects and reference to "the compound" includes reference to one or more compounds, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

As used herein, the terms "alkyl" and "alkenyl" include straight-chain and branched-chain monovalent hydrocarbyl radicals, and combinations of these, which contain only C and H when they are unsubstituted. Examples include methyl, ethyl, isobutyl, cyclohexyl, cyclopentylethyl, 2 propenyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl and alkenyl substituents contain 1-12C (alkyl) or 2-12C (alkenyl). Preferably they contain 1-8C (alkyl) or 2-8C (alkenyl). Sometimes they contain 1-4C (alkyl) or 2-4C (alkenyl). A single group can include more than one type of multiple bond, or more than one multiple bond; such groups are included within the definition of the term "alkenyl" when they contain at least one carbon-carbon double bond.

Alkyl and alkenyl groups are often substituted to the extent that such substitution makes sense chemically. Typical substituents include, but are not limited to, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R, SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl and alkenyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., —NR$_2$, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O or S) as a ring member.

As used herein, the term "cycloalkyl" encompasses a carbocyclic non-aromatic group that is connected via a ring carbon atom, and "cycloalkylalkyl" may be used to describe a carbocyclic non-aromatic group that is connected to the molecule through an alkyl linker. Similarly, the term "cycloalkenyl" may be used herein to describe a carbocyclic non-aromatic group that is connected via a ring carbon atom with one or more double bonds but not aromatic, and "cycloalkenylalkyl" may be used to describe a carbocyclic non-aromatic group that is connected to the molecule through an alkyl linker. The sizes and substituents that are suitable for the cycloalkyl, cycloalkylalkyl, cycloalkenyl, and cycloalkenylalkyl groups are the same as those described above for alkyl groups. As used herein, these terms also include rings that contain one or more double bonds, as long as the ring is not aromatic.

As used herein, "acyl" encompasses groups including an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

"Aromatic" moiety or "aryl" moiety refers to a monocyclic or fused bicyclic moiety having the well-known characteristics of aromaticity; examples include phenyl and naphthyl. Aryl and heteroaryl moieties may be substituted with a variety of substituents such as the substituents described above for "alkyl" and "alkenyl."

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof.

"Halo" as used herein includes fluoro, chloro, bromo and iodo.

2. Description

Computational Methods to Calculate Molecular Descriptors

The methods of the disclosure allows intelligent and rapid screening of untested volatile chemical space and chemical libraries by computationally identifying important characteristics shared between known active compounds, described by calculated molecular descriptors, circumventing many of the previously described obstacles.

The disclosure provides a chemical informatics method that identifies important structural features shared by ligands such as activating odors for individual odor receptors or olfactory neurons and utilizes these important features to screen large libraries of compounds in silico for novel ligands. These important structural features can also be used to increase understanding of breadth of tuning for each cognate of a ligand such as an odor receptor in chemical space and perform reverse chemical ecology in silico.

Although the methods of the disclosure have been exemplified using odor receptor and volatile chemical species. The method is also predictable to taste receptors, g-protein coupled receptors, ion gated channels, ligand gated channels and the like.

Structure-based clustering can be used to identify compounds useful in compositions of the disclosure. The algorithm can include linkage clustering to join compounds into similarity groups, where every member in a cluster shares with at least one other member a similarity value above a user-specified threshold.

The disclosure provides a structural basis of odorant molecule interaction with odor receptors through a novel chemical informatics platform. The disclosure provides a method to identify molecular structural properties that are shared between the activating odorants (actives) for an individual odor receptor. By identifying the molecular features shared by actives, the disclosure provides a system to perform in silico screens of large chemical space (100s of thousands to millions) to predict novel ligands for odor receptors or odor receptor neurons. This method can be applied in virtually any species where a training set of odorant responses is known for individual receptor or cellular level. The disclosure demonstrates this using a single unit electrophysiology to test a subset of the predictions in vivo. The data demonstrate that the method is very successful in predicting novel ligands.

The disclosure demonstrates the method can be modified to be able to predict ligands for narrowly-tuned receptors and neurons that are thought to be highly specialized, like pheromone receptors. In addition olfactory neurons whose response profiles are known, but whose odor receptors have not yet been decoded are provided. The method is also able to predict odorant ligands for two distinctly different classes of odor receptors. Insect odor receptors are proposed to be 7 transmembrane GPCR like proteins with inverse orientation in the membrane that function as either heteromeric ligand gated ion channels or cyclic-nucleotide activated cation channels. Mammalian odor receptors on the other hand are true GPCRs. The method is able to predict ligands for both insect and mammalian odor receptor classes. In addition to predicting ligands the disclosure also allows investigation of the coding of each tested receptor or receptor neuron in chemical space consisting of plant volatiles, fragrances and human volatiles.

Since different odor receptors can respond to vastly differing compound shapes and sizes it is unlikely that the full collection of molecular descriptors would be optimal for all receptors. Depending upon the unique structural features of active odors certain molecular descriptors may be better suited at describing characteristics of activating compounds for an individual receptor, and such descriptors can be identified from much larger sets by dimensionality reduction. Thus it is possible to greatly improve Or-specific descriptor space by identifying specific molecular descriptors from amongst the large collection that were best suited for each Or.

The disclosure provides a method of computationally screening a vast number of compounds to predict ligands (activators or inhibitors) for individual receptors or receptor expressing cells, wherein a known ligand or set of known ligands for a receptor or receptor expressing cell, either identified through electrophysiology, imaging assays, or binding assays, are used as a training set for selecting optimized molecular descriptors, which can subsequently be used to screen a large collection of untested compounds computationally to identify compounds that are structurally related to the known ligands, outputting the identified putative ligands to a user and exposing a receptor or receptor expressing cell to the putative ligand and determining either a change in spike frequency, florescence intensity, or binding affinity in the receptor or receptor expressing cell, wherein a change compared to baseline is indicative of a ligand for the receptor or receptor expressing cell.

The disclosure also provides a method of computationally screening a vast number of compounds to predict ligands (activators or inhibitors) for individual receptors or receptor expressing cells that have only one known strong activator or inhibitor, either identified through electrophysiology, imaging assays or binding assays, wherein a single known ligand from a receptor or receptor expressing cell is used to identify the structurally closest compounds in a chemical space made using several or all available structural descriptors, outputting the identified putative ligands to a user and exposing a receptor or receptor expressing cell to the putative ligand and determining either a change in spike frequency, florescence intensity, or binding affinity in the receptor or receptor expressing cell, wherein a change compared to baseline is indicative of a ligand for the receptor or receptor expressing neuron. In one embodiment, positives having a desired functional activity are used to further define the structural descriptors along with previously known activating odorants.

The disclosure also provides a method of computationally screening a vast number of compounds to predict compounds which cause a specific behavior (attraction, repellency, mating, aggression, or oviposition), wherein an compound or set of known compounds causing a specific behavior are used as a training set for selecting optimized molecular descriptors, which can subsequently be used to screen a large collection of untested odorants computationally to identify compounds that are structurally related to the known behavior modifying compounds, outputting the identified putative behavior modifying compounds to a user and testing the compounds for behavior modification, wherein a change compared to baseline behavior is indicative of a behavior modifying compound. In various embodiments, compounds are volatile odors and either the receptor is an odor receptor expressed by a specific neuron or cell type in a specific invertebrate species or receptor-expressing cells are odor receptor neurons present in a specific species of invertebrate.

In other embodiment, compounds are soluble ligands and either the receptor is a gustatory receptor expressed by a specific neuron or cell type in a specific invertebrate species or receptor-expressing cells are gustatory receptor neurons present in a specific species of invertebrate. In yet other embodiments, the compounds are volatile ligands and either the receptor is a gustatory receptor expressed by a specific neuron or cell type in a specific invertebrate species or receptor-expressing cells are gustatory receptor neurons present in a specific species of invertebrate. In further embodiments, the compounds are volatile odors and either the receptor is an odor receptor expressed by a specific neuron or cell type in a specific vertebrate species or receptor-expressing cells are odor receptor neurons present in a specific species of mammals. In some embodiments, the compounds are soluble ligands of volatile ligands and either the receptor is a gustatory receptor expressed by a specific neuron or cell type in a specific vertebrate species or receptor-expressing cells are gustatory receptor neurons present in a specific species of mammals.

As mentioned above, the methods of the disclosure can be used to screen ligands for a number of different biological molecules including GPCR. Accordingly, in one embodiment, the compounds are soluble or volatile ligands and either the receptor is a GPCR expressed by a specific neuron or cell type in a specific invertebrate or vertebrate species or receptor-expressing cells are GPCR expressing cells present in a specific species of invertebrate or vertebrate.

In yet other embodiment, the compounds are identified by the method of the disclosure and are identified as compounds for ligand gated ion channels. For example, the compounds can be soluble or volatile ligand and either the receptor is a ligand gated ion channel expressed by a specific neuron or cell type in a specific invertebrate or vertebrate species or receptor-expressing cells are ligand gated ion channel expressing cells present in a specific species of invertebrate or vertebrate.

The disclosure provides a method of identifying a ligand for a biological molecule including (a) identifying a known ligand or set of known ligands for a biological molecule, or identifying a compound which causes a specific biological activity, (b) identifying a plurality of descriptors for the known ligand or compound, (c) using a Sequential Forward Selection (SFS) descriptor selection algorithm to incrementally create a unique optimized descriptor subsets from the plurality of descriptors for the known ligand or compound, (d) identifying a putative ligand or compound that best-fits the unique optimized descriptor subset, and (e) testing the putative ligand or compound in a biological assay including the biological molecule wherein a change in activity of the biological molecule compared to the molecule without the putative ligand is indicative of a ligand the interacts with the biological molecule.

The disclosure utilizes in one embodiment a Sequential Forward Selection (SFS) descriptor selection method to incrementally create unique optimized descriptor subsets for each odor receptor. For example, starting with the combined group of 3424 descriptors from the full sets of Dragon and Cerius2 descriptors, an initial descriptor was selected whose values for the 109 odors showed the greatest correlation with activity for a specific Or. Additional descriptors were incrementally added to the growing optimized descriptor set based on their ability to further increase the Pearson correlation with activity for a specific Or. Each iteration increased the size of the optimized descriptor set for that Or by one. When a round of descriptor selection failed to increase the correlation between compound distance based upon the descriptor sets and those based upon known compound activity, the selection process was halted. As a result, optimized descriptor sets and their sizes are expected to vary across Ors.

In some embodiments, the molecular descriptors include the descriptors listed in FIG. 10. In some embodiments, the molecular descriptors include one or more descriptors selected from the group consisting of B05[C-N], EEig15r, B06[C-N], Mor07p, GVWAI-80, N-072, EEig12d, RDF055u, Mor32v, BELe6, O-060, J3D, RDF050u, EEig13r, and F03[C-N]. In other embodiments, the molecular descriptors include one or more descriptors selected from the group consisting of B05[C-N], EEig15r, B06[C-N], Mor07p, GVWAI-80, N-072, EEig12d, RDF055u, Mor32v, and BELe6. In other embodiments, the molecular descriptors include one or more descriptors selected from the group consisting of B05[C-N], EEig15r, B06[C-N], Mor07p, and GVWAI-80.

In some embodiments, the molecular descriptors include the descriptors listed in FIG. 11. In some embodiments, the molecular descriptors include one or more descriptors selected from the group consisting of B05[C-N], EEig15r, RDF055e, piPC10, F03[C-N], J3D, N-072, EEig15x, B06 [C-N], Mor27u, RDF040p, RDF055m, EEig12d, EEig15d, and Mor25e. In other embodiments, the molecular descriptors include one or more descriptors selected from the group consisting of B05[C-N], EEig15r, RDF055e, piPC10, F03 [C-N], J3D, N-072, EEig15x, B06[C-N], and Mor27u. In other embodiments, the molecular descriptors include one or more descriptors selected from the group consisting of B05[C-N], EEig15r, RDF055e, piPC10, and F03[C-N].

In some embodiments, the molecular descriptors include one or more descriptors selected from the group consisting of B05[C-N], piID, N-072, nRCONR2, RDF035v, EEig08r, D-Dr06, Mor10p, BAC, EEig14d, Mor27e, J3D, EEig12d, F04[C-N], DISPv, RDF035p, GVWAI-80, and STN. In other embodiments, the molecular descriptors include one or more descriptors selected from the group consisting of B05[C-N], piID, N-072, nRCONR2, RDF035v, EEig08r, D-Dr06, Mor10p, BAC, and EEig14d. In other embodiments, the molecular descriptors include one or more descriptors selected from the group consisting of B05[C-N], piID, N-072, nRCONR2, and RDF035v.

Using the principles above, an in silico method of compound identification and clustering was used to characterize potential receptor ligands. Since the Or-optimized descriptors can group highly active compounds tightly together in chemical space for each Or, this method can be used to rank untested compounds according to their distance from known actives. This allowed us to computationally screen a vast area of chemical space of potential volatiles in a very efficient and accurate manner.

The disclosure provides a chemical informatics method that identifies important structural features shared by activating or inhibiting odors for individual odor receptors or olfactory neurons and utilizes these important features to screen large libraries of compounds in silico for novel ligands. These important structural features can also be used to increase understanding of breadth of tuning for each Or in chemical space and perform reverse chemical ecology in silico.

Once one or more compounds have been identified using the computational methods described herein, the one or more compounds are tested in biological assays such as a trap assays or arm-in-cage assays, as discussed in more detail in Examples 2 and 3, below. In such assays, the one or more compounds are exposed to arthropods and the repellency of the one or more compounds is quantified.

Compounds and Compositions for Insect Repellents, Masking Agents, and Traps

The disclosure provides methods for identifying and the identified compositions of volatile odorants that modulate the electrophysiological response of neuron in various insect disease vectors including *Drosophila melanogaster*, *Culex quinquefasciatus*, *An. gambiae* and *Aedes aegypti* mosquitoes. In some embodiments, the odorants can completely inhibit the electrophysiological response of the neuron at very low concentrations.

The compounds and compositions of the disclosure can be used as antagonist to mask the chemo attractant activity for a particular odor receptor. Alternatively, the certain compounds may at as agonist in which they activate the receptor and stimulate the neuron. In such instances the compounds and compositions can be used as attractants alone or in combination with other materials depending upon the subject and purpose (e.g. an insecticide, trap, or other mechanical, electrical or chemical that kills the insect or prevents its escape). An antagonist refers to a compound that can reversibly or irreversibly inhibit that activity of a sensing neuron upon exposure to the compound such that the neuron ORN cannot properly signal upon a change in odor levels.

The disclosure provides chemicals that can be used as insect repellents and/or masking agents by virtue of their property to block a critical component of the host odor cue. The compounds are effective if they are capable of inhibiting the electrophysiological response of the neuron. The volatile compounds of the disclosure have masking and repellant effects by impairing the ability to find a host via long-range cues emitted from a typical target or subject (e.g., human breath).

In some embodiments, the repelling composition includes one or more compounds selected from the group consisting of methyl N,N-dimethyl anthranilate, ethyl anthranilate, butyl anthranilate, or 2,3-dimethyl-5-isobutyl pyrizine. In some embodiments, the repelling composition further includes one or more compounds from Table 1, below. In other embodiments, the repelling composition further includes one or more compounds from Table 2, below.

In some embodiments, the repelling composition includes one or more compounds listed in Table 2. In some embodiments, the repelling composition includes two or more compounds listed in Table 2.

In some embodiments, the repelling composition includes one or more compounds listed in Table 1. In some embodiments, the repelling composition includes two or more compounds listed in Table 1. In other embodiments, the repelling composition further includes one or more compounds listed in Table 2.

In some embodiments, the repelling composition includes two or more compounds listed in Table 1; two or more compounds listed in the Table 2; or two or more compounds selected from the group consisting of methyl N,N-dimethyl anthranilate, ethyl anthranilate, butyl anthranilate, or 2,3-dimethyl-5-isobutyl pyrizine.

In some embodiments, the repelling composition includes a compound of formula I:

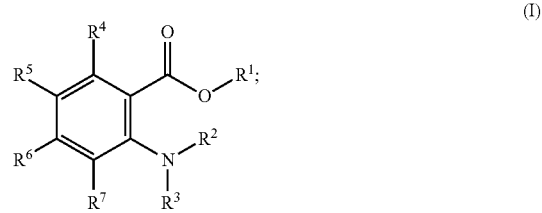

wherein:
$R^1$ is selected from the group consisting of H, C1-C12 alkyl, C2-C12 alkenyl, aryl, arylalkyl, cycloalkyl, cycloalkylalkyl, cycloalkenyl, and cycloakenylalkyl;

$R^2$ and $R^3$ are each independently selected from the group consisting of H, C1-C12 alkyl, benzoyl, cycloalkyl, cycloalkylalkyl, cycloakenyl, cycloakenylalkyl, arylalkyl, formyl, acyl, and $R^2$ and $R^3$ taken together form an =C—$R^8$;

$R^4$, $R^5$, $R^6$, and $R^7$ are each independently selected from the group consisting of H, C1-C4 alkyl, halo, and alkoxy; and $R^8$ is C1-C12 akyl, C2-C12 alkenyl, aryl, arylalkyl, cycloalkyl, cycloalkylalkyl, cycloakenyl, and cycloakenylalkyl. In some embodiments, $R^1$ is C1-C4 alkyl. In some embodiments, $R^1$ is $CH_3$, $CH_2CH_3$, or $CH_2CH_2CH_3$. In some embodiments, $R^1$ is $CH_3$, $CH_2CH_3$, or $CH_2CH_2CH_2CH_3$ and $R^2$ and $R^3$ is H. In some embodiments, the compound of formula I is methyl N,N-dimethyl anthranilate, ethyl anthranilate, or butyl anthranilate.

The odorants of the disclosure provide new and useful compositions for insect repellents, masking agents and traps. The compounds of the disclosure are useful in small quantities, can be delivered in multiple forms like vapors and lotions, are economical, environmentally friendly, and are present in natural sources. In some embodiments, the repelling composition is formulated as a lotion, cream, dust, cosmetic, perfume, spray, paste, slow-release granule, paint, treated clothing, treated netting, treated building material, or incense.

The compounds may be used alone or in combination with other agents. The compounds of the disclosure may be combined with additional active agent, insecticides and the like in traps to reduce the presence of amount of an insect in the environment. For example, compounds of the disclosure may be used in combination with insect traps (e.g., tape, combustibles, electric traps).

In yet a further embodiment, the compounds may be formulated for application to the skin, clothing or other material. The compounds of the disclosure can "mask" the location of a subject by antagonizing the receptor neurons of an insect etc. thereby inhibiting the ability to locate a prey.

For example, the compounds of the disclosure may be used as repellents or in compositions including said repellent compounds and the use of such repellent compounds and compositions in controlling pests. In some embodiments, the compounds and compositions are gustatory repellents (anti feedents). In some embodiments, the compounds may be applied to an article that is placed on or near humans, animals, and/or plants. In some embodiments, the compounds and compositions are applied to plants for organic farming applications. In other embodiments, the compounds or compositions are applied spatially or topically in areas to prevent the arthropods from venturing into such areas.

Liquid formulations may be aqueous-based or non-aqueous (e.g., organic solvents), or combinations thereof, and may be employed as lotions, foams, gels, suspensions, emulsions, microemulsions or emulsifiable concentrates or the like. The formulations may be designed to be slowly release from a patch or canister.

The compositions may include various combinations of compounds as well as varying concentrations of the compound depending upon the insect to be repelled or masked, the type of surface that the composition will be applied to, or the type of trap to be used. Typically the active ingredient compound of the disclosure will be present in the composition in a concentration of at least about 0.0001% by weight and may be 10, 50, 99 or 100% by weight of the total composition. The repellent carrier may be from 0.1% to 99.9999% by weight of the total composition. The dry formulations will have from about 0.0001-95% by weight of the pesticide while the liquid formulations will generally have from about 0.0001-60% by weight of the solids in the liquid phase.

As mentioned above, the compositions may be formulated for administration to a subject. Such formulations are typically administered to a subject's skin. The composition may also be formulated for administration to garments, belts, collars, or other articles worn or used by the subject from whom insects are to be repelled. The formulation may be applied to bedding, netting, screens, camping gear and the like. It will be recognized that the application of the compositions and compounds of the disclosure do not only include human subjects, but include canines, equines, bovines and other animals subject to biting insects. For topical application, the formulation may take the form of a spray formulation or a lotion formulation.

The compounds according to the disclosure may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, and the like, if desired, in the form of particular dosage preparations for specific application made therefrom, such as solutions, emulsions, suspensions, powders, pastes, and granules as described herein or as otherwise known in the art which are thus ready for use.

The repellent compounds may be administered with other insect control chemicals, for example, the compositions of the invention may employ various chemicals that affect insect behaviour, such as insecticides, attractants and/or repellents, or as otherwise known in the art. The repellent compounds may also be administered with chemosterilants.

In yet another aspect, the volatile compounds of the disclosure may be emitted from vaporizers, treated mats, cylinders, oils, candles, wicked apparatus, fans and the like when exposing the compound or compounds to the pests. A liquid source that can evaporate to form vapors may be used in barns, houses, or patios.

The disclosure also provides chemicals that can be used as bait to lure insects to traps by virtue of activating neurons. An advantage of these odorants will be their ability to be delivered in an economical and convenient form for use with traps. This function can be achieved by applying or locating the chemotractant compound of the disclosure near a suction based, or light based, or electric current based or other forms of trapping apparatus.

In order to verify whether the predictions discussed above were meaningful, functional evidence was obtained. In order to validate the success of the in silico predictions the responses of Odor receptors that respond to DEET were used. To test identified compounds any number of biological assays can be used to measure ORN activity in the presence of a putative ligand/compounds. For example, to demonstrate the activity of the compounds identified above, a single-unit electrophysiology test can be used for each predicted compound, resulting in a quantitative value of activation. Taken together these results demonstrate that the Or-optimized descriptor set based in silico screening of chemical space is extremely efficient at identifying volatile ligands for odor receptors. Based upon the data and chemical odorants identified herein, additional odorants can be identified using the structural information of the odorants, in silico modeling and screening and biological assays.

The disclosure provides a group of volatile chemicals that can be used to modify host-seeking behaviour by stimulating or inhibiting odor and taste receptors. The compounds of the disclosure are exposed to arthropods using a variety of methods, as discussed in more detail below and in the Examples. In some embodiments, the compounds are formulated as liquid compositions and placed in a container or on an article. In some embodiments, the compounds are formulated for application on human skin, on animals, or on plants. In some embodiments, the method of repelling an arthropod including exposing the arthropod with any of the repelling compositions disclosed herein. In some embodiments, the exposing the arthropod with the repelling composition is carried out using a vaporizer, evaporator, fan, heat, candle, or wicked apparatus. In some embodiments, the arthropod is an insect. In some embodiments, the arthropod is of the order Diptera. In some embodiments, the arthropod is of the genus *Drosophila*. In some embodiments, the arthropod is a mosquito. In some embodiments, the mosquito is of the species *Aedes aegypti*.

The disclosure also provides a method of inhibiting, preventing or reducing the incidence of insect-borne disease in a subject, the method including the step of over stimulating or antagonizing a receptor in an insect with a compounds or combination of compounds, wherein the receptor response is modified and attraction to the subject inhibited, thereby inhibiting, preventing or reducing the incidence of insect-borne disease in a subject.

In one embodiment, the disease is malaria, dengue, yellow fever, river blindness, lymphatic filariasis, sleeping sickness, leishmaniasis, epidemic polyarthritis, West Nile virus disease or Australian encephalitis.

The examples are illustrative. It will be recognized the use of specific odor receptors in the examples below can be substituted with any biological molecule that is capable or binds to a cognate/ligand. Such ligands can be small or large molecule organic molecules. The tables below are also illustrative. Each molecule in the table can be used independently in formulations, compositions or devices or may be used in combination. To describe each and every combination would be redundant to the general descriptions herein and one of skill in the art will recognize that the various individual compositions, the various receptors can be utilized by the methods and compositions of the disclosure.

The following examples are intended to illustrate but not limit the disclosure. While they are typical of those that might be used, other procedures known to those skilled in the art may alternatively be used.

EXAMPLES

Example 1

Identification of Compounds Based on Calculated Descriptors

A large panel of odors was assembled from multiple sources in order to train the platform to predict repellency. 34 n-acyl piperdines and 38 carboxamides, which have previously been directly tested for their duration of protection, were included in the training set. Eucalyptol, linalool, alpha-thuj one, and beta-thuj one, which had been tested for activity against the proposed DEET receptor, as well as Picaridin, which is widely used for repellency, were also included.

As these odors were tested using different approaches, a single unit of measure was needed to standardize them for training. Since the largest proportion of odors was measured in protection time, all odors were converted into this single standard of protection time in days to match with the Katritzky data at a concentration of 25 $\mu$mol/cm$^2$. Picaridin, which is believed to have a similar protection to DEET, was given the same protection time as DEET (17.5 days). Eucalyptol, linalool, alpha-thujone, and beta-thujone, all of which have shown similar activation to the proposed DEET receptive neuron, were also given the same protection time as DEET (17.5 Days). While this is a very rough approximation, it is sufficiently accurate for training.

As these repellent training odors represents a very focused chemical library and a structurally diverse dataset is ideal for identifying features that are important for a particular trait (i.e. repellency), a number of odors that are structurally unlikely to activate the same receptor as the repellent odors were also included. With these non-repellent odors added, the repellent training library consists of a broad collection of functional groups including alcohols, esters, acids, ketones, alkanes, aromatics, terpenes, and heterocycles.

Most repellent odors observed were predominately found in the n-acyl piperidine odor set. And that there were significant structural differences between this set of odors and the less repellent carboxamides. These distinct structural differences alter the outcome of the predictive platform. Due to this, the dataset of tested odors was dived into two distinct training sets. The first set includes all without the carboxamide odors. The second set includes all odors (FIG. 1).

Figure 3:
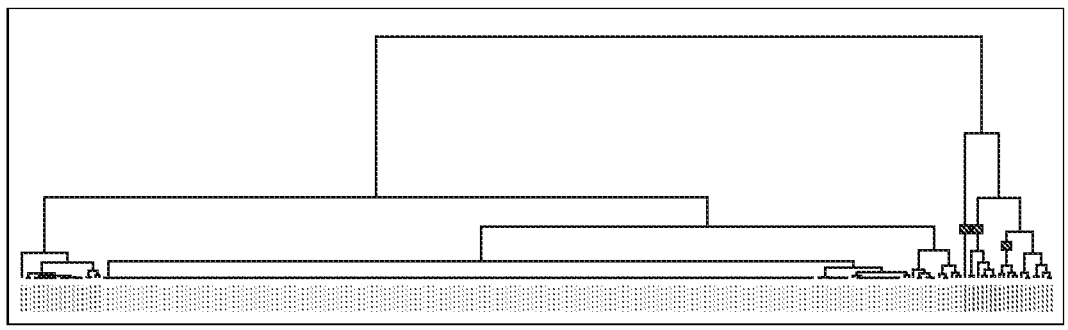
FIG. 3 depicts compound repellency classification through repellency clustering using a second training set.

Compounds were clustered using Euclidean distance and hierarchical clustering based on differences in repellency. Repellency is labeled below each branch of FIGS. 2 and 3 ranging from bright red (mostly far left in FIG. 2 and far right in FIG. 3), which denotes the most repellent, to gray, which indicates the least repellent. Compounds below the red square, which indicates a cut point, were classified as repellent. The cut point location was determined by best classification separation. Three different thresholds were tested including 17.5, 24.5, and 39.5 days. The final threshold was set at 39.5 days protection time.

Molecular descriptors are able to describe the structure of molecules through computationally derived values, which represent zero, one, two, or three-dimensional information of a compound. These descriptor type dimensionalities confer molecular information through classes such as constitutional, structural fragment, topographic, or spatial information, respectively. Comparison of molecular descriptors to describe highly active odorant structures has proven to be highly beneficial. In species where a specific behavior, such as avoidance, has been tested against a panel of odors it is possible to use molecular descriptors to identify novel potential ligands using the known actives as a training set. The 3-Dimensional structures were predicted using of the Omega2 software package. The commercially available software package Dragon (3,224 individual descriptors) from Talete was used to calculate molecular descriptors. Descriptor values were normalized across compounds to standard scores by subtracting the mean value for each descriptor type and dividing by the standard deviation. Molecular descriptors that did not show variation across compounds were removed.

Since different odor receptors, which are responsible for identifying behaviorally modifying odors, can respond to vastly differing compound shapes and sizes it is unlikely that a full collection of molecular descriptors would be optimal for identification of repellent odors. Depending upon the unique structural features of repellent odors certain molecular descriptors may be better suited at describing characteristics of activating compounds for interacting receptors, and such descriptors can be identified from much larger sets by dimensionality reduction. Thus it is possible to greatly improve behavior-specific descriptor space by identifying specific molecular descriptors from amongst the large collection that were best suited for repellency.

Figure 4:
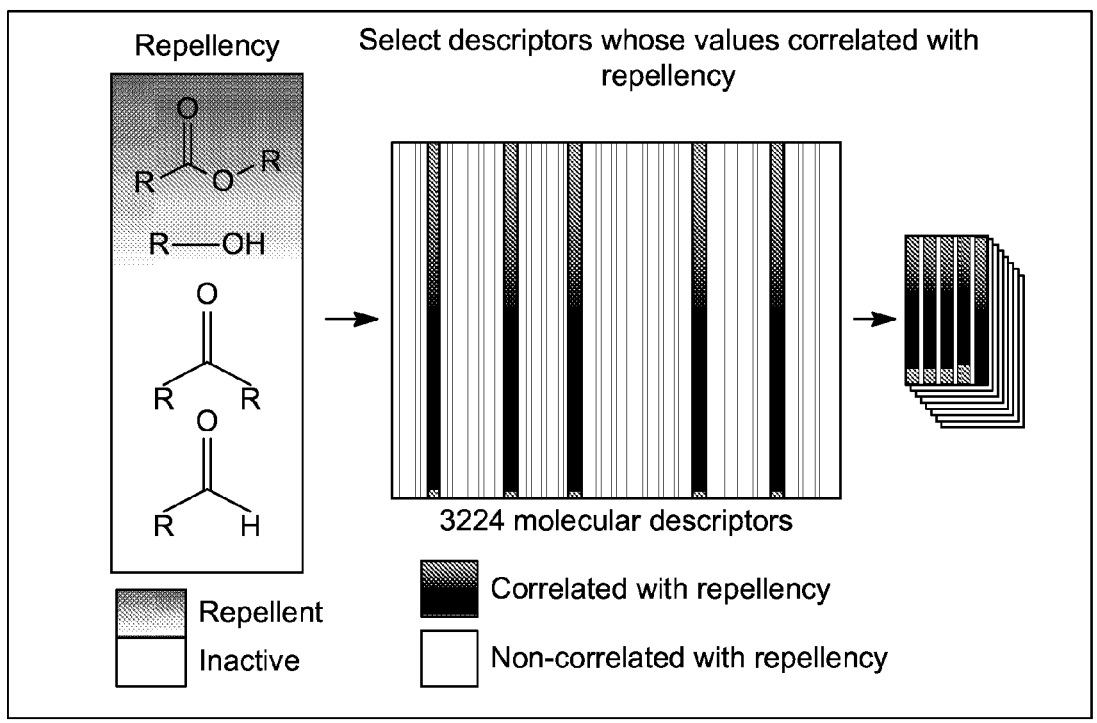
FIG. 4 is a graphic depicting the process for optimizing descriptor subsets for odor repellency.

A Sequential Forward Selection (SFS) descriptor selection method was used to incrementally create a unique optimized descriptor subset to describe repellency. Starting with the combined group of 3224 descriptors from the full set of Dragon descriptors, an initial descriptor was selected whose value showed the greatest correlation with repellency (FIG. 4). Additional descriptors were incrementally added to the growing optimized descriptor set based on their ability to further increase the Pearson correlation with activity for repellency. Each iteration increased the size of the optimized descriptor set by one. When a round of descriptor selection failed to increase the correlation between compound distance based upon the descriptor sets and those based upon known compound activity, the selection process was halted. As a result, optimized descriptor set and their sizes are expected to vary for different datasets.

Training sets 1 and 2 (FIG. 1) were used for optimized descriptor set selection. Each combination resulted in a unique optimized descriptor set. The ability of each of these optimized sets to describe repellency in the training set was then compared.

Figure 5:
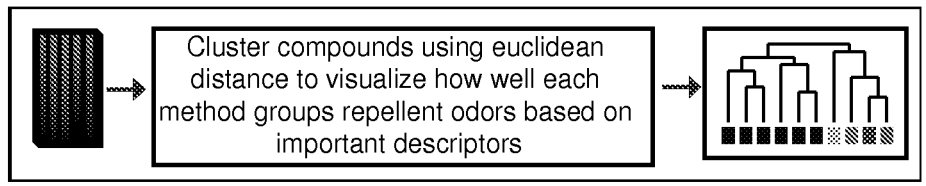
FIG. 5 is flow diagram depicting the process of obtaining a best optimized descriptor set.

Odors were clustered for each optimized descriptor set by applying hierarchical clustering and Euclidean distance. The optimized molecular descriptor sets were compared individually and in combinations for their ability to group repellent odors from the training set (FIG. 5).

An optimized set of descriptors was then identified which best described the repellency of training set 1. Many repellency thresholds and optimized descriptor sets were compared for their ability to identify highly repellent odors, as previously stated (FIGS. 4, 5). The premier optimized descriptor system resulted from a union of two optimized descriptor sets. The goal was to create a system where the most highly repellent odors had the maximum separation from non-repellent odors based on important structural features. Thus features were identified that the highly repellent odor have that are not shared with either less repellent odors from the Katritzky et al. and Leal et al. datasets or the non-repellent odors from the Hallem et al. and Carey et al. datasets. The system which best achieved this was the joining of two unique optimized systems, one which separated the highly repellent odors from the non-repellent odors and another which separated highly repellent odors from the less repellent odors. The first included system was identified by using protection times at 25 $\mu$mol/cm$^2$, a repellency threshold of 39.5 days, and all four datasets. The second included system was again identified using protection times at 25 $\mu$mol/cm$^2$, a repellency threshold of 39.5 days, and all four datasets, however this time only Katritzky odors with repellency times of greater than 39.5 days were included for training. When these two optimized descriptor sets were combined and the resulting system was used for clustering (FIG. 4), the highly repellent odors were brought more closely together than was found using all other tested training sets.

The optimized set of descriptors which best described the repellency of training set 2 were identified. Many repellency thresholds and optimized descriptor sets were compared for their ability to identify highly repellent odors, as previously stated (FIGS. 4, 5). The premier optimized descriptor system resulted from a union of two optimized descriptor sets. The goal was to create a system where the most highly repellent odors had the maximum separation from non-repellent odors based on important structural features. Thus features that the highly repellent odor have that are not shared with either less repellent odors were identified from the Katritzky et al. and Leal et al. datasets or the non-repellent odors from the Hallem et al. and Carey et al. datasets. The system which best achieved this was the joining of two unique optimized systems, one which separated the highly repellent odors from the non-repellent odors and another which separated highly repellent odors from the less repellent odors. The first included system was identified by using protection times at 25 $\mu$mol/cm$^2$, a repellency threshold of 39.5 days, and all four datasets. The second included system was again identified using protection times at 25 $\mu$mol/cm$^2$, a repellency threshold of 39.5 days, and all four datasets, however this time only Katritzky odors with repellency times of greater than 39.5 days were included for training. When these two optimized descriptor sets were combined and the resulting system was used for clustering (FIG. 4), we found the highly repellent odors were brought more closely together than was found using all other tested training sets.

Figure 8:
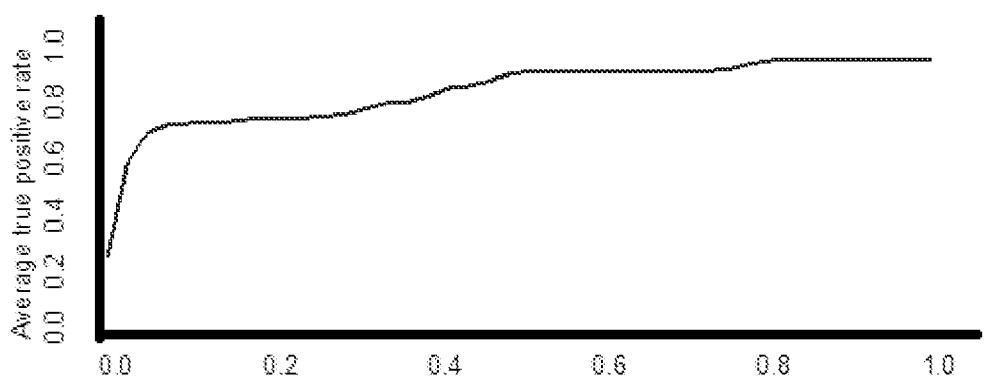
FIG. 8 is a graph showing computational validation of optimized descriptor set for training set 1.

A 5-fold cross-validation was performed for training set 1 by dividing the training into 5 equal sized partitions. During each run, one of the partitions is selected for testing, and the remaining 4 sets are used for training. The training process is repeated 5 times with each unique odorant set being used as the test set exactly once. For each training iteration a unique set of descriptors was calculated from the training compound set. These descriptors were then used to calculate minimum distances from the test set compounds to the closest active exactly as we use to predict ligands in our ligand discovery pipeline. Once test set compounds have been ranked by distance from closest to furthest to a known repellent odor in the training set, a receiver operating characteristics (ROC) analysis is used to analyze the performance of the computational ligand prediction approach (FIG. 8).

Figure 9:
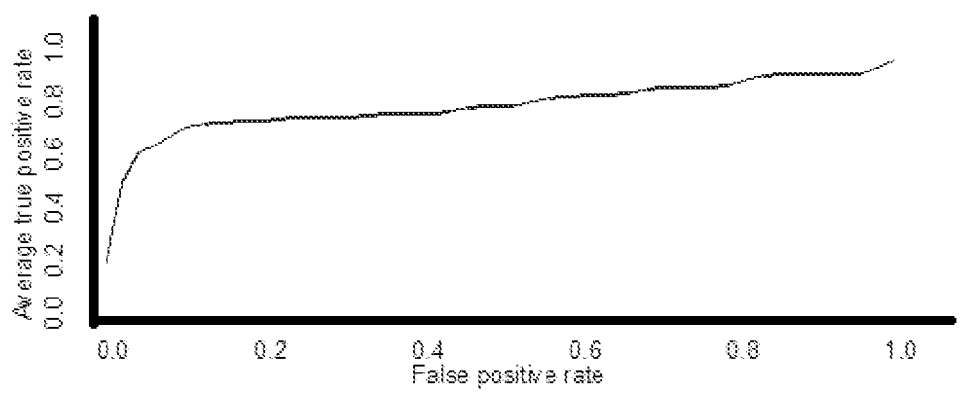
FIG. 9 is a graph showing computational validation of optimized descriptor set for training set 2.

A 5-fold cross-validation was performed for training set 2 by dividing the training into 5 equal sized partitions. During each run, one of the partitions is selected for testing, and the remaining 4 sets are used for training. The training process is repeated 5 times with each unique odorant set being used as the test set exactly once. For each training iteration a unique set of descriptors was calculated from the training compound set. These descriptors were then used to calculate minimum distances from the test set compounds to the closest active exactly as we use to predict ligands in our ligand discovery pipeline. Once test set compounds have been ranked by distance from closest to furthest to a known repellent odor in the training set, a receiver operating characteristics (ROC) analysis is used to analyze the performance of the computational ligand prediction approach (FIG. 9).

The optimized descriptor subsets calculated for training set 1 are described in FIGS. 1, 2, 4, 5, and 6. Optimized descriptor occurrences, symbol, brief description, class and dimensionality are listed in FIG. 10. Descriptors are listed in ascending order of when they were selected into the optimized set. Weights indicate the number of times a descriptor was selected in an optimized descriptor set.

The optimized descriptor subsets calculated for training set 2 are described in FIGS. 1, 2, 4, 5, and 6. Optimized descriptor occurrences, symbol, brief description, class and dimensionality are listed in FIG. 11. Descriptors are listed in ascending order of when they were selected into the optimized set. Weights indicate the number of times a descriptor was selected in an optimized descriptor set.

Figure 12:
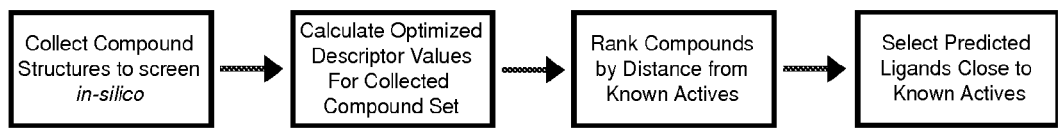
FIG. 12 shows a flow diagram for high-throughput in-silico screening of >400,000 compounds.

Since the repellency-optimized descriptors can group highly active compounds tightly together in chemical space, once can use this method to rank untested compounds according to their distance from known repellents (FIG. 12). This allowed a computationally screen of a vast area of chemical space of potential volatiles in a very efficient and accurate manner. Greater than 400,000 different putative volatile compounds were screened for repellency. This would be entirely unfeasible using current behavioral assay technology.

Figure 6:
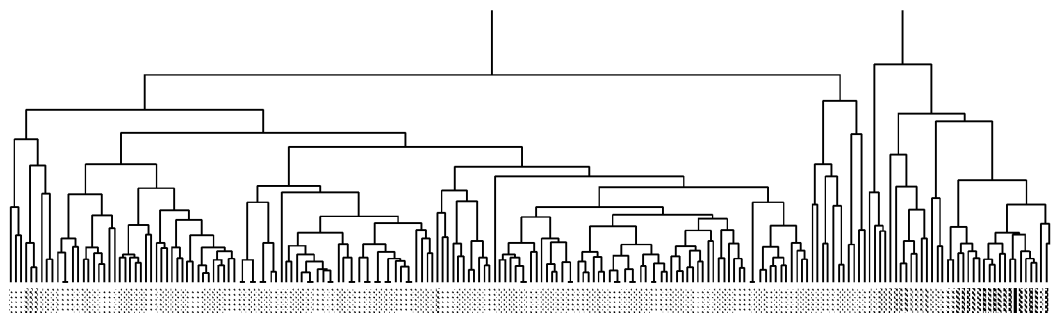
FIG. 6 shows a system in which the best-described repellency for training set 1 was a union of two unique optimized descriptor sets.
Figure 7:
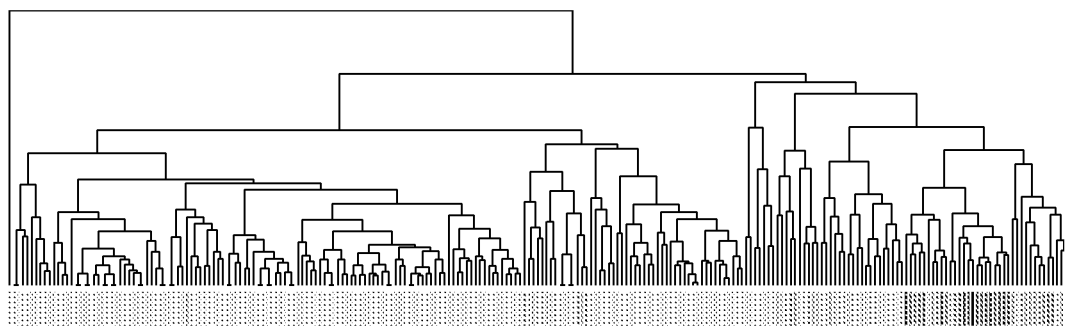
FIG. 7 shows a system in which the best-described repellency for training set 2 was a union of two unique optimized descriptor sets.

A large collection of potential chemosensory compounds were amassed using criteria from known odors, such as molecular weight <325 and atom types limited to C, O, N, S, & H. Using these criteria over 400,000 compounds were obtained along with their structures. We then calculated distances in chemical space for each of the >400,000 compounds individually using each of the previously determined repellency-optimized descriptor sets (FIGS. 6, 7). In this fashion the large collection of unknown chemicals were sorted by distances from each of the odors considered as repellent from the training odors. Euclidean distance was used as a similarity measure. Using this system the untested odors in the 400,000 compound library were ranked according to their closeness to the known repellents from each training set individually. The top hits in this large chemical space, that are found in natural sources, are listed below in Table 1. These predictions could prove to be extremely valuable, providing a putative list of chemicals with repellent properties.

TABLE 1

| SMILES STRUCTURE | CAS NUMBER |
|---|---|
| O=C(N1C)N(C)C2=C(C=CC=C2)C1=O | 1013-01-0 |
| O=C(C)CC(NC1=CC=CC=C1)=O | 102-01-2 |
| O=CNC1=CC=CC=C1 | 103-70-8 |
| C=CC1(C)C(C(C)=C)CC(C(C)=C)CC1 | 11033-44-6 |
| CC1CC(C=C(C2C1CC(=C(C)C)C2)C)OC(=O)C | 117-98-6 |
| CC(C)(C)C(C)C(C)C | 1186-53-4 |
| CC1=CC=C([N+]([O-])=O)C=C1[N+]([O-])=O | 121-14-2 |
| NC(OCC)=O | 121382-27-2 |
| CC1COCC2=CC3=C(C=C12)C(C(C3(C)C)C)(C)C | 1222-05-5 |
| COC1=NC=CN=C1C(C)CC | 123625-20-7 |
| O=C(C(N12)=NC3=C(C=CC=C3)C1=O)C4=C2C=CC=C4 | 13220-57-0 |
| NC1=CC=CC=C1C(OCCC2=CC=CC=C2)=O | 133-18-6 |
| CC(NCCC(C)C)=O | 13434-12-3 |
| CC(C)(C)CC(C)CC(C)(C)C | 13475-82-6 |
| O=C(OC(C)(C1CC=C(C)CC1)C)C2=CC=CC=C2N | 14481-52-8 |
| CC1CC(C2=C(C1(C)C)C=C(C(=C2)C(=O)C)C)(C)C | 1506-02-1 |
| CC1=CCC(CC1)(C(C)CCC=C(C)C)O | 15352-77-9 |
| OC(C)C(OC1C(C(C)C)CCC(C)C1)=O | 17162-29-7 |
| CC1CCC(CC2=C1CCC2C)C(C)(C)OC(=O)C | 17431-48-0 |
| C=CC1(C)C(C(C)=C)C=C(C(C)C)CC1 | 20307-84-0 |
| O=C1C(C)(C)CC(CC1C)=O | 20547-99-3 |
| C1(CCCC2=CC=CC=C2)=NC=CC=C1 | 2110-18-1 |
| CC1=CCC(CC1)C2(CCC(C(O2)(C)C)O)C | 22567-36-8 |
| S=C=NCCC1=CC=CC=C1 | 2257-09-2 |
| O=C1NCCC1 | 22580-55-8 |
| CN1C(C2=NC=CC=C2)CCC1 | 23950-04-1 |
| COC1=NC=CN=C1CC(C)C | 24683-00-9 |
| O=C(OC)C1=CC=CC=C1NC(C)=O | 2719-08-6 |
| CC(C)C(OCC1=CCC2CC1C2(C)C)=O | 29021-37-2 |
| CC1=C(C=C(C=C1)[C@H](C)CCC=C(C)C)O | 30199-26-9 |
| CC(=C1CCC(C(C1)C(=C)C)(C)C=C)C | 3242-08-8 |
| O=C(OC)CC1=CC=C(C(C)(C)C)C=C1 | 33155-60-1 |
| CC1C2CC(C1(C)C)CC2C3CCCC(C3)O | 3407-42-9 |
| O=C(OCC)C1=CC=CC=C1NC | 35472-56-1 |
| O=C(N(CC)CC)COC1=CC=CC=C1 | 3613-97-6 |
| O=C1N=C(N)NC2=NC=C(C(O)C(O)C)N=C12 | 36183-24-1 |
| O=C(N)NC(C(N1)=O)NC1=O | 37305-69-4 |
| O=C(OCC)C1=CC=CC=C1NCC | 38446-21-8 |
| O=C(OC)C1=CC=CC=C1NC=O | 41270-80-8 |
| CC1(C)C(O1)CCC(C)(OC(C)=O)C=C | 41610-76-8 |
| O=C1SC2=CC=CC=C2N1 | 4464-59-9 |
| CCCCCCCCCC(N1CCCCC1)=O | 46910-28-5 |
| CC1=C(C(CCC1)(C)C)CC=O | 472-66-2 |
| CC1CCC2C1C3C(C3(C)C)CCC2(C)O | 489-41-8 |
| CC1=CC(=C(C=C1)C(C)(C)C)O)C(C)(C)C | 50356-19-9 |
| OC1=CC=C(C(C)(C)C)C=C1C(C)(C)C | 50356-26-8 |
| CCCCC1=NC=C(C)N=C1C | 50888-63-6 |
| C/C=C\C1=C(OC)C=C(OC)C(OC)=C1 | 5273-86-9 |
| O=C(/N=N/C(N)=O)N | 52737-71-0 |
| CCCCCCCCC(N1CCOCC1)=O | 5299-64-9 |
| CCCCCCCC(N1CCOCC1)=O | 5338-65-8 |
| CC(/C=C/C1C(C)=CCC(C)C1(C)C)=O | 54082-69-8 |
| C=CC(C)(C)C(C=C(C)C)=O | 546-49-6 |
| CC(NCC(C)CC)=O | 54824-90-7 |
| CN1C(CCC1)C2=CC=CN=C2 | 551-13-3 |
| CC1=CCC(CC1)C2(CCC(O2)C(C)C)O)C | 55399-12-7 |
| CC1OC2(C(CCCC2(C)C)(OC(C)=O)C)CC1 | 57893-27-3 |
| O=C(O)C1=CC=CC=C1NC(C2=CC=CC=C2)=O | 579-93-1 |
| C=CC(O)(C)CCC1C(CCC2C(C)(C)CCCC12C)=C | 596-85-0 |

TABLE 1-continued

| SMILES STRUCTURE | CAS NUMBER |
|---|---|
| CC(N)=O | 60-35-5 |
| CC1CN(C(C2CCCCC2)=O)CCC1 | 63441-20-3 |
| NC1=CC=CC=C1C(OC2=CC=C3C=CC=CC3=C2)=O | 63449-68-3 |
| NC1=CC=CC=C1C(OCC/C=C\CC)=O | 65405-76-7 |
| O=C(OCC(C)C)C1=CC=CC=C1NC | 65505-24-0 |
| O=C(O)C(N)CCC(N)=O | 6899-04-3 |
| O=C1C/C(C)=C/CC/C(C)=C/CC1=C(C)C | 6902-91-6 |
| CC1=C2C=CC=CC2=NC=N1 | 700-46-9 |
| NC1=CC=CC=C1C(OCC=C)=O | 7493-63-2 |
| NC1=CC=CC=C1C(OC2CCCCC2)=O | 7779-16-0 |
| NC1=CC=CC=C1C(OCC(C)C)=O | 7779-77-3 |
| CC(NC)=O | 79-16-3 |
| O=C(/C=C/C1C(C)=CCCC1(C)C)CCC=C | 79-78-7 |
| O=CC(C)CC1=CC=C(C(C)(C)C)C=C1 | 80-54-6 |
| CC1(SC(SC(S1)(C)C)(C)C)C | 828-26-2 |
| O=C(N1C)N(C)C=CC1=O | 874-14-6 |
| CC(O)(C1=CC=C(C)C=C1)CCC=C(C)C | 92691-77-5 |
| O=C1NNC=N1 | 930-33-6 |
| CC(C)=CC1C(C(OCC)=O)C1(C)C | 97-41-6 |

A second library of compounds was screened using the chemical informatics methods described herein. The top hits of putative repellent compounds are listed below in Table 2. These top hits were predicted based upon optimized molecular descriptor values as described in the claims from a collected set of 12,050 compounds present in the U.S. Food and Drug Administration Everything Added to Food in the Unites States Database (FDA EAFUS), Volatile Compounds in Food Database (VCF), European Commission of Health and Consumers Database (CosIng), Sigma Flavor and Fragrances, Pherobase, Goodscents, and Knudsen, J. T., Eriksson, R., Gershenzon, J. & Stahl, B. Diversity and Distribution of Floral Scent. The Botanical Review 72, 1-120 (2006).

TABLE 2

| SMILES STRUCTURE | CAS NUMBER |
|---|---|
| O=C(NC1C(C)CCCC1)C2=C(F)C(F)=C(F)C(F)=C2F | 1003050-32-5 |
| C1=CC=CC(=C1C(OC)=O)N(C)C | 10072-05-6 |
| C1(C2=CC=CC=C2)=NC=CC=C1 | 1008-89-5 |
| CC1=NC(CCCC)=C(C)N=C1C | 10132-38-4 |
| CCCCCC1=NC(C)=C(C)N=C1C | 10132-42-0 |
| CC(C)CCC1=C(C)N=C(C)C(C)=N1 | 10132-43-1 |
| CC1NC(CCCC)SC(C)S1 | 101517-79-7 |
| CC1NC(C)SC(CCCC)S1 | 101517-81-1 |
| CC1NC(C)SC(CC(C)C)S1 | 101517-87-7 |
| C1=CC=C(C=C1)NC(CC(C)=O)=O | 102-01-2 |
| CCCC1=C(C)N=C(CC)O1 | 102586-53-8 |
| CC1=C(CC)OC(C(C)C)=N1 | 102586-54-9 |
| CC1=NC=CN=C1C2=CC=CO2 | 104593-66-0 |
| CC1=NC(CCCC)=C(CCCC)O1 | 104638-08-6 |
| CCCCC1=C(CCCC)N=CO1 | 104638-12-2 |
| CCCCC1=C(CC)N=C(C)O1 | 106100-43-0 |
| CC(C1=NC(C)=C(CC)O1)C | 106100-44-1 |
| CCCC1=NC=C(CC)N=C1C | 107054-27-3 |
| C1=C(C(=CC=C1O)NC(/C=C/C2=CC=C(O)C=C2)=O)C(=O)O | 108605-70-5 |
| CC1=C(SC=[N+]1CC2=CN=C(N=C2N)C)CCO | 108631-50-1 |
| CCC(NCC(C)(C)COC1=C2C(N)=NS(NC2=CC=C1)(=O)=O)=O | 1093200-92-0 |
| CC1=CN=C(CCC(C)C)C(C)=N1 | 111150-30-2 |
| CC(C)C[C@@H](C(OCC)=O)NC(C)=O | 1114-55-2 |
| O=C(C1[C@H](C(C)C)CC[C@@H](C)C1)NC2=CC=C(CC(N)=O)C=C2 | 1119711-29-3 |
| O=C(O)C(C1=CC=CC=C1NC(C)=O)COC | 1190427-41-8 |
| O=C(N1C(CCO)CCCC1)OCC(C)C | 119515-38-7 |
| CC1=CC(C)=NC2=CC=CC=C12 | 1198-37-4 |
| O=C1NC2=C(C(C)=C(C)S2)C(N)=N1 | 121746-18-7 |
| C1=C(CC(NC(C)=O)C(O)=O)C2=C([NH]1)C=CC=C2 | 1218-34-4 |
| C1(NC2=CC=CC=C2)=CC=CC=C1 | 122-39-4 |
| O=C(N)N=NC(=O)N | 123-77-3 |
| C(C1=CCC2C(C1C2)(C)C)CO | 128-50-7 |
| C=C(C)/C=C/C1OCCC=C(C)C1 | 130021-98-6 |
| C=C(C)/C=C/[C@H]1OCCC[C@@H](C)C1 | 130021-99-7 |
| C=C(C)/C=C/[C@H]1OCCC[C@H](C)C1 | 131320-18-8 |
| C1=NC2=C(C(=C1)C(C)C)C=CC=C2 | 1333-53-5 |
| C1=CC=CC2=NC=CC(=C12)CC(C)C | 1333-58-0 |
| CC1=C2N=CC=C(C)C2=CC=C1 | 13362-80-6 |
| C1=CC(=CC2=CC=CN=C12)C(C)C | 135-79-5 |
| CC(O1)=CC=C1CN2C=CC=C2 | 13678-52-9 |
| O=CC1=CC=CN1CCC(C)C | 13678-79-0 |
| [C@@H]2(C(OC1=CC=C(O)C=C1)=O)CCC(N2)=O | 138506-45-3 |

TABLE 2-continued

| SMILES STRUCTURE | CAS NUMBER |
|---|---|
| N[C@@H](CC1=CC=C(C=C1)O)C(O)=O | 140-43-2 |
| CC(C1=CC(C(C)=O)=NC=C1)C | 142896-09-1 |
| C=C(C1=CC(C(C)=O)=NC=C1)C | 142896-11-5 |
| C=C(C1=NC=CC(C(C)=O)=C1)C | 142896-12-6 |
| CC1=CC=CN1CC2=CC=CO2 | 1438-95-5 |
| C(C(C(NCC(O)=O)=O)N)CSC | 14486-03-4 |
| O=C(NCC(C)C)/C=C/CCC1=CC=C(OCO2)C2=C1 | 145398-89-6 |
| OC(SC(O)C(N)=O)C(N)=O | 14618-65-6 |
| C1=CC(=CC=C1OC)C=NC2=C(C=CC=C2)C(=O)OC | 14735-72-9 |
| CC1=NC=C(C(CO)=C1O)COC([C@H](CO)N)=O | 14942-12-2 |
| C1=CC=CC=C1CC(C(O)=O)N | 150-30-1 |
| C1=C(NC(=O)N)C=CC(=C1)OCC | 150-69-6 |
| C(O)C2CC1C(C)(C)C1C=C2C | 15103-32-9 |
| O=C(N1)C2=CC=CC(CCCC)=C2C1=O | 1515-72-6 |
| CC(N(CCCC)CCCC)=O | 1563-90-2 |
| CC1=NC(CCCC)=CN=C1C | 15834-78-3 |
| CCC(C)CC1=CN=CC(C)=N1 | 159664-01-4 |
| CCCCCC1=NC=CN=C1C | 15987-02-7 |
| S=C1(CC2=CC=CO2)C=NC=CN1 | 164352-93-6 |
| [C@@H](NC(=O)CC[C@@H](C(=O)O)N)(C(=O)O)CCCCN | 17105-15-6 |
| O=C(O)[C@H](CC1=CC=CC=C1)NC(/C=C/CCCCCCCC)=O | 175357-18-3 |
| O=C(OCC)C(N)CC1=CC=CC=C1 | 1795-96-6 |
| CCC(N(CC)C1=CC=CC(C)=C1)=O | 179911-08-1 |
| CC(C(N1)=CC2=C1C=CC=C2)(C)C | 1805-65-8 |
| C1=C(C(OC(C)C)=O)C(=CC=C1)N | 18189-02-1 |
| C1=CC(=C(C=C1)C(=O)OCCCCCCC)N | 18189-05-4 |
| CC1=CN=C(C)C(CCC(C)C)=N1 | 18433-98-2 |
| CC(C)CCC1=CN=C(C)C(C)=N1 | 18450-01-6 |
| CCC(C)CC1=C(C)N=C(C)C(C)=N1 | 18482-80-9 |
| C1=CC=C(N=C1COC(NC)=O)COC(NC)=O | 1882-26-4 |
| C(NC(=O)\C=C\C=C\CCCCC)C(C)C | 18836-52-7 |
| O=C1C=C(C2=CC=CC=C2)C=CN1 | 19006-81-6 |
| C(NC(=O)CCCCCCCCC=C)CO | 20545-92-0 |
| CC(C1=NC2=CC=CC=C2S1)CCC | 20614-71-5 |
| CC1=C(CCCCCC)OC(C)=N1 | 20662-85-5 |
| CC1=C(CCCCCC)N=C(C)O1 | 20662-86-6 |
| CC1=C(C)N=C(CCCCCC)O1 | 20662-87-7 |
| C2=C(C1=NC=CO1)C=CC=C2 | 20662-88-8 |
| C1=CC=CC(=N1)CCCCCCC | 20815-27-4 |
| N=C(N)NCCC[C@@H](C(O)=O)NC(C)=O | 210545-23-6 |
| CC1(C(C(C(=CCC1)C)\C=C\C(C)O)C | 211241-68-8 |
| C[C@@H](C(OC)=O)NC(CCCCCCCCCCC)=O | 21539-57-1 |
| C1=C(C)C=CC2=C1C(CCC2)=O | 22009-37-6 |
| CC1(C(=C(CCC1)C)\C=C\C(O)C)C | 22029-76-1 |
| C1=CC=C2C(=C1OC)C=CC=C2 | 2216-69-5 |
| C1=C(CC(NC(C(CC(O)=O)N)=O)C(OC)=O)C=CC=C1 | 22839-47-0 |
| O=C(O)[C@H](CC1=CNC=N1)NC(C)=O | 2407-02-1 |
| C1=NC(=C(OC)N=C1)C(CC)C | 24168-70-5 |
| O=C(N(CC)CC)CC1=CC=CC=C1 | 2431-96-1 |
| C1=C(C=CC(=C1OC)O)CNC(CCCCCCCC)=O | 2444-46-4 |
| CCCCCCC/C=C/C=C/C(NCC(C)C)=O | 24738-51-0 |
| O=C(N)CC[C@@H](C(O)=O)NC(C)=O | 2490-97-3 |
| C(C(O)C)N1CN(CN(C1)CC(O)C)CC(O)C | 25254-50-6 |
| O=C(NCSS)C1=CC=CC=C1 | 2527-58-4 |
| C(C(NC(=O)\C=C\C=C\CC\C=C\C)C)C | 25394-57-4 |
| S=C(N1)NC2=C(NC=N2)C1=O | 261-31-4 |
| CC1=C(C)N=C(CC(C)C)O1 | 26131-91-9 |
| S=C=NCCCC1=CC=CC=C1 | 2627-27-2 |
| O=C1C(CCCCCCCC)=NSC1 | 26530-20-1 |
| C(N1C(=O)N(C(C1=O)(C)C)CCO)CO | 26850-24-8 |
| CCC1=CC2=CC=C=C2N=C1O | 2721-59-7 |
| CC1=CC=C(C(N(CC)CC)=O)C=C1 | 2728-05-4 |
| C1=CC=CC2=CC=C(N=C12)C | 27601-00-9 |
| CC1=CN=C(C2=CC=CO2)C=N1 | 27610-38-4 |
| O=C(N1CCCCC1)/C=C/C2=CC=CC=C2 | 27845-72-3 |
| C1=NC=CN=C1CCCCCC | 28217-91-6 |
| N#C/C=C/C1=CC=C(OC)C=C1 | 28446-68-6 |
| C1=C(C(OCCC(C)C)=O)C(=CC=C1)N | 28457-05-8 |
| NCC(N(CCCCCCCCCCCC)C)=O | 287735-50-6 |
| C1=C(C(=CC=C1)C(OCCCCC)=O)N | 30100-15-3 |
| C1=CC=C(C=C1)C2OC(CC(C2)=C)C | 30310-41-9 |
| NC(CC1=CC=CC=C1)C(O)=O | 30394-07-1 |
| O=C(N1)C2=CC=CC(C(C)C)=C2C1=O | 304-17-6 |
| [C@H](NC(CCN)=O)(CC1=CN=C[NH]1)C(O)=O | 305-84-0 |
| C1=CC=CC(=C1C(OCCC)=O)N | 30954-98-4 |
| CC1=NC(C(C)CC)=CN=C1C | 3226-30-0 |
| C1(CC/N=C/C2=CC=CC=C2)=CC=CC=C1 | 3240-95-7 |
| O=C(O)CC(N1)=CC2=C1C=CC=C2 | 32536-43-9 |

TABLE 2-continued

| SMILES STRUCTURE | CAS NUMBER |
|---|---|
| CC1=CN=C(C)C(CC(C)C)=N1 | 32736-94-0 |
| CC1=CN=CC(C2=CC=CO2)=N1 | 32737-03-4 |
| CC1=NC=CN=C1CCC(C)C | 32737-06-7 |
| CCCCCC1=CN=C(C)C=N1 | 32737-07-8 |
| CCC(C)CC1=NC=CN=C1C | 32737-08-9 |
| CCCCCC1=NC=CN=C1OC | 32737-12-5 |
| C1=C(C=CC(=C1)CC#N)C(C)(C)C | 3288-99-1 |
| C(C1=C(CCCC1(C)C)C)CC(O)C | 3293-47-8 |
| [O-]/[NH+]=C(C1=CC=CC=C1)/C(C)(C)C | 3376-24-7 |
| N[C@@H](CC1=CC=C(C=C1)O)C(OCC)=O | 34081-17-9 |
| C1=CC=CC=C1C(CCCC)C#N | 3508-98-3 |
| [C@H]12C(=CC[C@H](C1(C)C)C2)CCO | 35836-73-8 |
| C2=C(OC1=CC=CC=C1)C=CC=C2C | 3586-14-9 |
| CC1=NC(C2=CC=CO2)=CN=C1C | 36238-34-3 |
| C1=C(N=CC(=N1)OC)CC(C)C | 36330-05-9 |
| C1=CC=C[N+](=C1SSC2=[N+](C=CC=C2)[O-])[O-] | 3696-28-4 |
| N[C@@H](CCCNC(N)=O)C(O)=O | 372-75-8 |
| C1=C(C(=CC=C1)N=CC2=CC=CC=C2)C(OC)=O | 37837-44-8 |
| C1=NC2=C(O1)CCCCCCCCC2 | 38303-23-0 |
| C1=CC=CC=C1C(OCC)=O)NCC | 38446-21-8 |
| C1=CN=CC=C1CC\C=C(\CCC=C(C)C)C | 38462-23-6 |
| CC1=NC=C(CC(C)C)N=C1C | 38888-81-2 |
| CCCCCC1=CN=C(C)C=C1 | 39161-35-8 |
| [C@@H](NC(=O)[C@@H](N)C)(C(=O)O)CCC(=O)N | 39537-23-0 |
| OC(C=C1)=CC=C1C[C@@H](C(O)=O)NC(CN)=O | 39630-46-1 |
| C(NC(C1C(CCC(C1)C)C(C)C)=O)C | 39711-79-0 |
| CC(C)=CCCC(C)CC1OCCN1C(C)=O | 39785-81-4 |
| C1=C(C=CC(=C1OC)O)CNC(CCCC\C=C\C(C)C)=O | 404-86-4 |
| CCC(CC)C(N(C)C1=CC=CC(C)=C1)=O | 406488-30-0 |
| CC1=CN=C(C)C(CCCC)=N1 | 40790-29-2 |
| CC2(C1CCC(O)(CC1=CCC2)C)C | 41199-19-3 |
| [C@@H]1(NC(=O)CC1)C(OCC(CC)CCCC)=O | 4261-80-7 |
| CC(C)CC1=C(C)N=C(C)C(C)=N1 | 46187-37-5 |
| CCCCCCCCCC(N1CCC(C)CC1)=O | 4629-14-5 |
| C1=CC=CC=C1CNCCCO | 4720-29-0 |
| C1=NC2=C([N]1CC(CO)O)C(N(C)C(N2C)=O)=O | 479-18-5 |
| C1=CC=CC(=C1N(C(\C=C\C)=O)CC)C | 483-63-6 |
| C(C([N+](C)(C)C)C([O-])=O)C1=CNC(N1)=S | 497-30-3 |
| O=C1C(C2=CC=CC=C2)=C(C)C(O)=CN1 | 49744-73-2 |
| NCCC1=CNC2=CC=C(C=C12)O | 50-67-9 |
| OC[C@@H]1[C@H](C[C@H](N2C(NC(C(C)=C2)=O)=O)O1)O | 50-89-5 |
| CC1=CC=C(C)N1CC2=CC=CO2 | 5049-47-8 |
| C1=C(C(=CC=C1)N=CC(CCC)C)C(OC)=O | 50607-64-2 |
| N1(CCC2=CC=CC=C2)C=CC=C1 | 50691-29-7 |
| CCCCCC1=NC=C(C)N=C1C | 50888-62-5 |
| OC1=C(O)C=CC(C(CNC)O)=C1 | 51-43-4 |
| CC(C(NC)=O)(C(C)C)C(C)C | 51115-67-4 |
| C(NC(=O)C(C(C)C)(C(C)C)CC)C | 51115-70-9 |
| CCC(CC)(CC)C(NC(C)(C)CO)=O | 51115-77-6 |
| NCCCC[C@@H](C(O)=O)NC(CCCCCCCCCCC)=O | 52315-75-0 |
| OCCC1=CNC2=C1C=CC=C2 | 526-55-6 |
| O=C(N1CCCCC1)C2CC=CCC2 | 52736-58-0 |
| N[C@@H](CC1=CC=CC=C1)C(O)=O | 5297-02-9 |
| NN(C1=CC=CC=C1)C2=CC=CC=C2 | 530-50-7 |
| C1=CC(=CC2=C1N=C(C)O2)C | 53012-61-6 |
| C1=CC=CC=C1CC\C=C/C#N)C | 53243-59-7 |
| C1=CC=CC=C1CC\C=C\C#N)C | 53243-60-0 |
| C1=CC=C2C(=N1)C=CC(=C2)CCCC | 53452-65-6 |
| CCCCCCC(N1CC(C)CCC1)=O | 53662-21-8 |
| C1=C(CC(NC(C)=O)C(O)=O)C=CC(=C1)O | 537-55-3 |
| CC1OCCC2=C(C(=O)NC=C12)C=O | 53848-05-8 |
| OC1=CC=C(CCN(C)C)C=C1 | 539-15-1 |
| CCCC1=C(C2=CC=CC=C2)C=NC=C1 | 53911-35-6 |
| O=C(N(CO)C1(CO)N2CO)N(CO)C1NC2=O | 5395-50-6 |
| N[C@@H](CC1=CNC2=CC=CC=C12)C(O)=O | 54-12-6 |
| C1=C(CCC(CC#N)C)C=CC=C1 | 54089-83-7 |
| CC1=CN=C(C2=CC=CO2)C(C)=N1 | 54300-11-7 |
| CC1=CN=C(C)C(C2=CC=CO2)=N1 | 54300-12-8 |
| CC1=CC=C(C2=NC=CN=C2C)O1 | 54300-13-9 |
| CC1=CC=C(C2=CN=C(C)C=N2)O1 | 54300-14-0 |
| CC1=CC=C(C2=CN=CC(C)=N2)O1 | 54300-15-1 |
| CC1=COC(C2=NC=CN=C2C)=C1 | 54300-16-2 |
| CC1=COC(C2=CN=CC(C)=N2)=C1 | 54300-17-3 |
| CC1=COC(C2=CN=CC(C)=N2)=C1 | 54300-18-4 |
| CC(C)CC1=CN=C(C)C(C)=N1 | 54410-83-2 |
| C[C@]1(C(C)C)CC=C[C@H](OCC)C1 | 54982-75-1 |
| O=C(O)[C@H](CC1=CNC2=CC=CC=C12)NO | 56-69-9 |
| C1=C(CC(NC(CCNC(C)=O)=O)C(=O)O)[NH]C=N1 | 56353-15-2 |

TABLE 2-continued

| SMILES STRUCTURE | CAS NUMBER |
|---|---|
| CCCCCC1=NC(C)=CN=C1C | 56617-69-7 |
| CCC(C)CC1=NC=C(C)N=C1C | 56617-70-0 |
| C1=CC(=CC2=C1OC(=N2)C)C | 5676-58-4 |
| CCC1(C(=O)NC(=O)NC1=O)CC | 57-44-3 |
| C(C1=C(C=CCC1(C)C)C)CC(O)C | 57069-86-0 |
| O=C(C1C(C(C)C)CCC(C)C1)NC2=CC=C(OC)C=C2 | 57233-03-1 |
| C1=CC=C(C=C1)C(=O)NC2=C(C=CC=C2)C(=O)O | 579-93-1 |
| O=C(N(C1=O)C)N(C2=C1N(C=N2)C)C | 58-08-2 |
| CN(C(N1C)=O)C2=C(NC=N2)C1=O | 58-55-9 |
| C(C2C1C(NC(N1)=O)CS2)CCCC(O)=O | 58-85-5 |
| OC[C@@H]1[C@H]([C@H]([C@H](N2C(NC(C=C2)=O)=O)O1)O)O | 58-96-8 |
| [C@H](NC(=O)CCN)(CC1=CN=C[N]1C)C(=O)O | 584-85-0 |
| CC(C1=NC2=CC=CC=C2N1)C | 5851-43-4 |
| C1=C(C(=CC=C1CC(C(O)=O)N)O)O | 59-92-7 |
| C1=CN=C(C(=N1)SCC2=CC=CO2)C | 59035-98-2 |
| C1=CC(=CC=C1CC(C(O)=O)N)O | 60-18-4 |
| C2=C(C1OCC=C(C1)C)C=CC=C2 | 60335-71-9 |
| C1(CC2=CC=CC=C2)CCCCO1 | 60466-73-1 |
| O=C1N(C)C2=C(C=CC=C2)C=C1 | 606-43-9 |
| CC/C=C\CC/C=C/C(NC1CC1)=O | 608514-55-2 |
| CC/C=C\CC/C=C/C(NCC)=O | 608514-56-3 |
| NCCC1=CNC2=CC=CC=C12 | 61-54-1 |
| C1=C(C)C=CC2=CC=CN=C12 | 612-60-2 |
| C2=CC=C1N=CC=CC1=C2C(C)(C)C | 61702-91-8 |
| CCCCCCC/C=N/N(C=O)C | 61748-13-8 |
| CC(C)C/C=N/N(C=O)C | 61748-18-3 |
| CCCCC/C=C\C=N\N(C=O)C | 62121-49-7 |
| CCCCC/C=C/C=N/N(C=O)C | 62121-50-0 |
| CC1CCN(C(C2CCCCC2)=O)CC1 | 62972-64-9 |
| O=C(O)C(N)CC1=CC=C(O)C(O)=C1 | 63-84-3 |
| C1=CC(=CN=C1)CCCCCCC | 6311-92-8 |
| CC2(C1C(=CC(O)(CC1)C)CCC2)C | 643-53-8 |
| CCC1N(C(C2CCCCC2)=O)CCCC1 | 64498-16-4 |
| [C@H]2(OC(=O)[C@H]1NC(=O)CC1)[C@@H](CC[C@@H](C)C2)C(C)C | 64519-44-4 |
| CCCC1=CC2=CC=CC=C2N=C1 | 64828-52-0 |
| CC1=CC=CN=C1C2=CC=CC=C2 | 64828-54-2 |
| OC[C@@H]1[C@H]([C@H]([C@H](N2C(N=C(C=C2)N)=O)O1)O)O | 65-46-3 |
| O=C(C1=CC(NC(N1)=O)=O)O | 65-86-1 |
| O=C(N(C1=O)C)N(C2=C1N(C=N2)C)CC(O)=O | 652-37-9 |
| C1=CC=CC(=C1C(OCC\C=C/CC)=O)N | 65405-76-7 |
| C1=CC(=CC2=CC=CN=C12)C(CC)C | 65442-31-1 |
| CCCC1=CC=NN1C2=CC=CC=C2 | 65504-93-0 |
| CC(C1=NC2=CC=CC=C2S1)CCCC | 65718-88-9 |
| O=CC1=CC=C(C)N1CC(C)C | 66054-34-0 |
| O=C(NC1=CC=CC=C1O)C2=CC=CC(O)=C2O | 66612-11-1 |
| CC2(C1=C(CC(O)(CC1)C)CCC2)C | 670-24-6 |
| C1=CC=C2C(=N1)C(=CC=C2)C(CC)C | 67634-06-4 |
| C1=CC=CC(=C1N=CCC2=CC=CC=C2)C(OC)=O | 67785-76-6 |
| C1=CC=CC(=C1C(OC)=O)N=CCC(CC(C)(C)C)C | 67801-42-7 |
| C1=CC=C(C=C1)N=CCCCCCCCC(=O)OC | 67801-44-9 |
| C1=CC=C(C=C1)N=C\C=C(C)\CCC=C(C)C)C(=O)OC | 67801-47-2 |
| C1=C(C(=CC=C1)N=CCC(CCC=C(C)C)C)C(=O)OC | 67845-42-5 |
| C1=C(C(OC\C=C(\CCC=C(C)C)C)=O)C(=CC=C1)N | 67859-99-8 |
| C1=C(N=C(=N1)CC(C)C)OC | 68039-33-8 |
| C1=CC=C(C=C1)C2OC(CC(=C2)C)C | 68039-40-7 |
| CC1C=C(C)CC(O1)C2=CC=CC=C2 | 68039-41-8 |
| CC(C2C(OC(=O)C1NC(=O)CC1)CC(CC2)C)C | 68127-22-0 |
| C1=C(C(C)(C)C)C=CC2=NC=CC=C12 | 68141-13-9 |
| C1=C(CC(C)C)C=CC2=C1C=CC=N2 | 68141-26-4 |
| CC1CC2(OC=C1)CCCCC2 | 68228-06-8 |
| C1=CC=CC(=C1C(=O)OCC)NCC2C(=C(CC2)C)C | 68228-09-1 |
| C1=C(C=CC2=C1C=CC(=N2)CC)CC | 68228-10-4 |
| C1=CC=C(C=C1C(C=O)CC)CC | 68228-11-5 |
| CCOC(C1=CC=C(C=C1)C)(C)C | 68279-51-6 |
| CC1=CC2C(C#N)CC1CC2C(C)C | 68311-05-7 |
| C1=CC2=C(C=C1)C(CCC2)CCO | 68480-12-6 |
| O=C([C@H]1[C@H](C(C)C)CC[C@@H](C)C1)NC2=CC=C(OC)C=C2 | 68489-09-8 |
| C1=C(C(=CC=C1)N\C=C2/CCC(=CC2C)C)C(=O)OC | 68738-99-8 |
| C1=NC(=C(N=C1)OC)CCCC(C)C | 68844-95-1 |
| C1=C(C(=CC=C1)N=CC2CCC(=CC2C)C)C(=O)OC | 68845-02-3 |
| O=C(N1)NC2=C(NC=N2)C1=O | 69-89-6 |
| O=C(O)C(N)CC1=CNC2=C1C=CC=C2 | 6912-86-3 |
| CC1N(C(C2CC=CCC2)=O)CCCC1 | 69462-43-7 |
| O=C(O)C1=CC=CC(C2=CC=CC=C2O)=C1NC(CC)=O | 697235-49-7 |
| CC(C1=NC2=CC=CC=C2S1)CCCCC | 69938-51-8 |
| C(C(C(NCC(=O)O)=O)NC(CCC(C(O)=O)N)=O)S | 70-18-8 |
| CC1=C2C=CC=CC2=NC(C)=N1 | 703-63-9 |
| CC1=CN=C(CC(C)C)C(C)=N1 | 70303-42-3 |

TABLE 2-continued

| SMILES STRUCTURE | CAS NUMBER |
|---|---|
| CCCCCC1=NC=C(CCCC)C=C1CCCC | 7033-69-4 |
| CC1OC2(C=C1)C(=CCC(C2C)C)C | 71078-31-4 |
| C1=CC=CC(=C1C(OC(CCC=C(C)C)(C=C)C)=O)N | 7149-26-0 |
| C1=C(C(=NC(=N1)OCC)OCC)C | 7193-87-5 |
| CC1=C(/C=C/C#N)C(CCC1)(C)C | 72214-33-6 |
| CCC(C)CC1=NC(C)=CN=C1C | 72668-36-1 |
| C1=CN=C(C(=N1)OCC)C(C)C | 72797-16-1 |
| CC1(C2=C(CCC1)CCC(C#N)C2)C | 72928-51-9 |
| C1=CC=CC2=C1C(=C[NH2]CC(C(O)=O)N | 73-22-3 |
| O=C(C)NCCC1=CNC2=CC=C(C=C12)OC | 73-31-4 |
| O=C(C1C(C(C)C)CCC(C)C1)NC2CC2 | 73435-61-7 |
| O=C(C1CC1)NC/C=C(C)/CCC=C(C)C | 744251-93-2 |
| O=C(C1=CC=C(OCO2)C2=C1)NC(CCC)CCC | 745047-51-2 |
| O=C(NCC1=CC=C(C)C=C1OC)C(NCCC2=NC=CC=C2)=O | 745047-97-6 |
| CCCCC1=NC2=CC=CC=C2C=C1 | 74808-78-9 |
| CCC(C)CC1=CN=C(C)C(C)=N1 | 75492-01-2 |
| CC1=NC=C(CCC(C)C)N=C1C | 75492-04-5 |
| O=C1OCCN1CCCCCCCCCC | 7693-82-5 |
| N#CCC1=CNC2=C1C=CC=C2 | 771-51-7 |
| CCCC1=C(CC)N=C(CC)O1 | 77311-03-6 |
| C1=CC=CC(=C1C(OCCCC)=O)N | 7756-96-9 |
| C(C(C(C(C(NCCC(N)=O)=O)O)(C)C)O | 7757-97-3 |
| C1=CC=CC(=C1C(OCC(C)C)=O)N | 7779-77-3 |
| OC(C=C1)=CC=C1CCNC(C(C)O)=O | 781674-18-8 |
| COC1=NC=C(CC(C)C)N=C1C | 78246-20-5 |
| CC1=CC=C(C)N1CCC(C)C | 78368-70-4 |
| CC1=CN(CC2=CC=CO2)C=C1 | 78368-71-5 |
| CC(C=CO1)=C1CN2C=CC=C2 | 78368-72-6 |
| CC(O1)=CC=C1CN2C(C)=CC=C2 | 78368-73-7 |
| CC1=C(C)N(CC2=CC=CO2)C=C1 | 78368-74-8 |
| CC1=CC=C(CC)N1CC2=CC=CO2 | 78368-75-9 |
| CC1=CC(C)=C(C)N1CC2=CC=CO2 | 78368-76-0 |
| O=CC1=CC=CN1CC2=CC=C(C)O2 | 78368-77-1 |
| OCC(C)(C)C(O)C(NCCC(O)=O)=O | 79-83-4 |
| CCCC(CC)CC1=NC=CO1 | 79886-43-4 |
| CC(O)/C=C/C1C(C)=CC=CC1(C)C | 79925-79-4 |
| CC(O)/C=C/C1C(C=CCC1(C)C)=C | 79925-80-7 |
| CC(O)C#CC1=C(C)C=CCC1(C)C | 79925-81-8 |
| CC1=CC(OCC)[C@]2([H])C[C@@]1([H])C2(C)C | 80581-06-2 |
| [C@H](C(NCCCO)=O)(C(CO)(C)C)O | 81-13-0 |
| C2=C(C1(CC(C)OC1)C)C=CC=C2 | 82461-14-1 |
| CN1C=NC(N(C(N2)=O)C)=C1C2=O | 83-67-0 |
| CC1=C(CC)N=C(C(C)C)O1 | 84027-96-3 |
| CC1=NC(CC)=C(CCCC)O1 | 84027-98-5 |
| CC1=C(CC)OC(CCCC)=N1 | 84028-02-4 |
| CC1=C(CC)N=C(CCCC)O1 | 84028-03-5 |
| CC(C1=NC=CO1)CC(C)CC | 84028-05-7 |
| CC(C1=NC=CO1)CC(C)CCC | 84028-13-7 |
| CC1=C(CC)OC(CCCCCC)=N1 | 84028-19-3 |
| C1=C(N(C(C(CC)C)=O)C)C=CC=C1 | 84434-18-4 |
| CC1CCC(C(C)C)C(C(NCCC2=NC=CC=C2)=O)C1 | 847565-09-7 |
| C1=CC=CC(=C1C(OC)=O)NC | 85-91-6 |
| N=C1OON(C2=CC=C(C1)C(C1)=C2O)C1 | 85058-43-1 |
| CCCC1=CN=C(C2=CC=CC=C2)C=C1 | 85237-77-0 |
| CC1=CN=C(C(OCC)C)C=N1 | 85985-31-5 |
| C1=CC=CC(=C1C2=CC=CC=C2)OC | 86-26-0 |
| CCCCCC1=NC(C)=C(C)S1 | 86290-22-4 |
| C1=CC=CC(=C1C(OCC)=O)N | 87-25-2 |
| C1=CC=CC2=C1C(=C[NH2]CC(O)=O | 87-51-4 |
| [C@@H](CSC(C1=C(C=CC=C1)O)=O)(NC(C)=O)C(O)=O | 87573-01-1 |
| CC1=CC=C2N=C(C)C=CC2=C1 | 877-43-0 |
| C1=CC=CC=C1CCNC(C)=O | 877-95-2 |
| CC(O)(O)C(NN(OC)S(=O)(C1=CC=CC=C1)=O)=O | 881993-56-2 |
| CC1=C(CCCC)OC(CCCC)=N1 | 88300-08-7 |
| CC(C)C(C(C)C)(C)C(NCCO)=O | 883215-02-9 |
| CC1CC(C)(C)C(C2=NC=CC=C2)CC1 | 885702-72-7 |
| CC1=CN=C(CCC(C)C)C=N1 | 90846-19-8 |
| C2=C(C(C1=CC=CC=C1)O)C=CC=C2 | 91-01-0 |
| C1=C(C)C=CC2=C1CCCN2 | 91-61-2 |
| C1=C(C)C=CC2=NC=CC=C12 | 91-62-3 |
| CC1=CN=CC(CCC(C)C)=N1 | 91010-41-2 |
| CC(C)C/C=N/CCC1=CC=CC=C1 | 92195-46-5 |
| CCCC1=NC(C)=C(C)N=C1C | 92233-82-4 |
| C1=C2C(=CC=C1OC)C=CC=C2 | 93-04-9 |
| C1=C2C(=CC=C1OCC)C=CC=C2 | 93-18-5 |
| C1=CC2=C(N=C1CC(C)C)C=CC=C2 | 93-19-6 |
| N=C(NC(N)=N)NC1=CC=CC=C1C | 93-69-6 |
| CC1(OCC2C(C1)CC(=C(C2)C)C)C | 94022-01-2 |

TABLE 2-continued

| SMILES STRUCTURE | CAS NUMBER |
|---|---|
| C1=CN=C(C(=N1)OCC\C=C\CC)C | 94159-29-2 |
| C2=C(C1OCCC(C1)C)C=CC=C2 | 94201-73-7 |
| O=C(N(CC)CC)C1=CC=CC(C)=C1 | 94271-03-1 |
| C1=CC=CC(=C1C(OCC\C=C\CC)=O)NC(=O)C | 94333-66-1 |
| CCC1=C(CC)N=C(CCCC)O1 | 94794-08-8 |
| CCCC1=C(C)OC(CCCC)=N1 | 94794-09-9 |
| O=C(C1CC1)NC2C(C(C)C)CCC(C)C2 | 958660-02-1 |
| CCCC1=CSC(CCCC)=N1 | 96693-89-9 |
| CCCCCC1=C(C)N=C(C)S1 | 96693-91-3 |
| N#CC(C=C)(C)CC1=CC=CC=C1 | 97384-48-0 |
| CC1=NC=C(CCCC)N=C1C | 97485-49-9 |
| CC1=NC=CN=C1CCCCC | 97485-50-2 |
| CCC(N1)=CC2=C1C=CC=C2 | 97542-81-9 |
| C(N(C(CCCCCC)=O)CC)C | 996-97-4 |

Example 2

Olfactory Avoidance Trap Assay for *Drosophila*

Four compounds identified in Example 1 were tested in trap assays along with DEET: butyl anthranilate (BA); ethyl anthranilate (EA); methyl N,N-dimethyl anthranilate (MDA); and 2,3-dimethyl-5-isobutyl pyrizine (DIP). Traps were made with two 1.5 ml microcentrifuge tubes (USA Scientific), 200 ul pipette tips (USA Scientific), and each cap contained standard cornmeal medium. A T-shaped piece of filter paper (Whatman #1) was impregnated with 5 ul of acetone (control) or 5 ul of 10%, 1%, 0.10% test odor, diluted in acetone. Traps were placed within a petri dish (100×15 mm, Fisher) containing 10 ml of 1% agarose to provide moisture. Ten flies wCs 4-7 days old were used per trial which lasted 48 hours. At the 48 hour time point, nearly all flies in the assays had made a choice. The 24 hour time point data was considered only if 30% of flies had made a choice, at 48 hours the majority of flies had made a choice. The results are shown in FIG. 13. Preference Index=number of flies in treated trap/(number of flies in treated+control traps).

Example 3

Arm-in-Cage Avoidance Assay for *Aedes aegypti*

Figure 14:
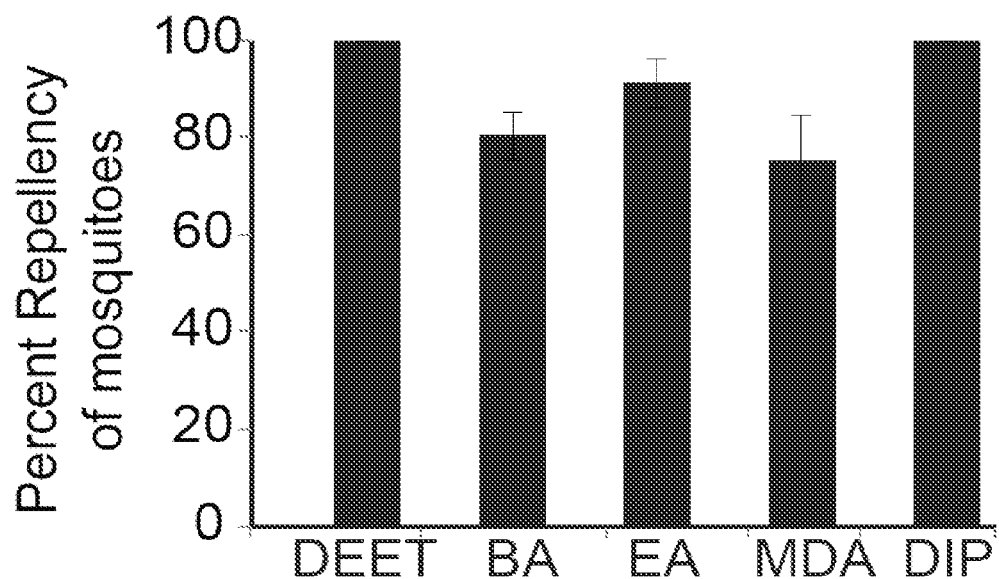
FIG. 14 shows the results of an arm-in-cage avoidance assay with female *Aedes aegypti* mosquitoes. The cumulative percentage of repellency is summed across minutes 2, 3, 4 and 5 of indicated treatment (10%), in comparison to the appropriate solvent control. N=5 trials/treatment, 40 mosquitoes/trial. (DEET=N,N-diethyl-3-methylbenzamide; BA=butyl anthranilate; EA=ethyl anthranilate; MDA=methyl N,N-dimethyl anthranilate; DIP=2,3-dimethyl-5-isobutyl pyrizine; Percentage Repellency=100×[1− (mean cumulative number of mosquitoes on the window of treatment for 5 seconds at time points 2, 3, 4, 5 min/mean cumulative number of mosquitoes that remained on window of solvent treatment for 5 seconds at time points 2, 3, 4, 5 min)]).
Figure 15:
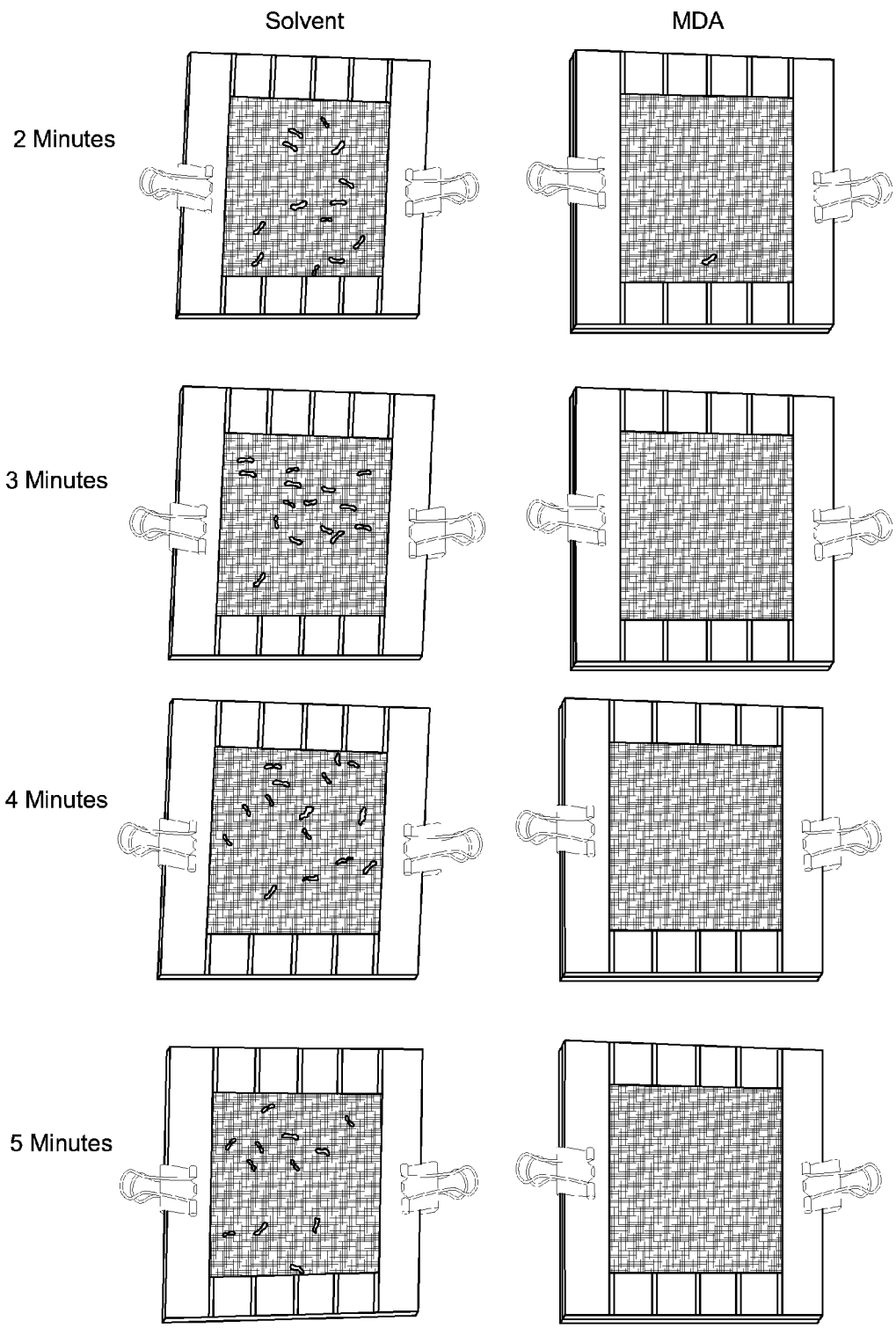
FIG. 15 shows representative still photographs from specific time-points of video assaying landing of female *Aedes aegypti* on solvent treated and MDA treated netting in the hand-in-glove assay. (MDA=methyl N,N-dimethyl anthranilate).

Four compounds identified in Example 1 were tested in arm-in-cage assays along with DEET: butyl anthranilate (BA); ethyl anthranilate (EA); methyl N,N-dimethyl anthranilate (MDA); and 2,3-dimethyl-5-isobutyl pyrizine (DIP). Repellency was tested in mated and starved *Aedes aegypti* females. A gloved hand with an opening exposing skin odorants protected by 2 layers of netting was presented to mosquitoes for 5 min inside a cage and video taped for landing and avoidance responses. Mosquitoes were unable to bite due to the outer protective layer of netting and the inner layer of netting was treated with either test compound (10%) or solvent, such that mosquitoes were able to respond to volatiles but unable to make physical contact. For contact version of the assay, the outer layer of netting was treated with DEET or solvent. The number of mosquitoes present for more than 5 seconds, and the numbers departing during the same period were counted from the videos at minutes 2, 3, 4, and 5 mins and repellency percentage and escape index calculated by comparing with similar numbers in solvent treated controls. Percentage Repellency=100×[1−(mean cumulative number of mosquitoes on the window of treatment for 5 seconds at time points 2, 3, 4, 5 min/mean cumulative number of mosquitoes that remained on window of solvent treatment for 5 seconds at time points 2, 3, 4, 5 min)]. The results are shown in FIGS. 14 and 15.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of repelling an arthropod, comprising exposing the arthropod to a repelling composition, wherein the repelling composition comprises at least one compound of formula I:

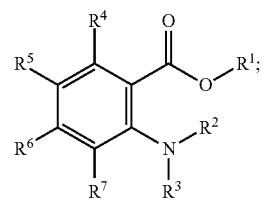

(I)

wherein:
$R^1$ is selected from the group consisting of C6-C12 alkyl, C4-C12 alkenyl, aryl, and arylalkyl;
$R^2$ and $R^3$ are each independently selected from the group consisting of H, C1-C12 alkyl, benzoyl, cycloalkyl, cycloalkylalkyl, cycloalkenyl, cycloakenylalkyl, arylalkyl, formyl, acyl, and $R^2$ and $R^3$ taken together form an =C—$R^8$;
$R^4$, $R^5$, $R^6$, and $R^7$ are each independently selected from the group consisting of H, C1-C4 alkyl, halo, and alkoxy; and
$R^8$ is selected from the group consisting of C1-C12 alkyl, C2-C12 alkenyl, aryl, arylalkyl, cycloalkyl, cycloalkylalkyl, cycloakenyl, and cycloakenylalkyl.

2. The method of claim 1, wherein:
$R^1$ is selected from the group consisting of C6-C12 alkenyl, aryl, and arylalkyl;
$R^2$ and $R^3$ are each H; and
$R^4$, $R^5$, $R^6$, and $R^7$ are each independently selected from the group consisting of H, C1-C4 alkyl, halo, and alkoxy.

3. The method of claim 1, wherein the at least one compound of Formula 1 is

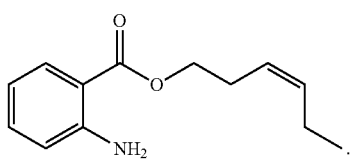 [SMILES: CC/C=C\CCOC(=O)c1ccccc1N]

4. The method of claim 1, wherein the at least one compound is

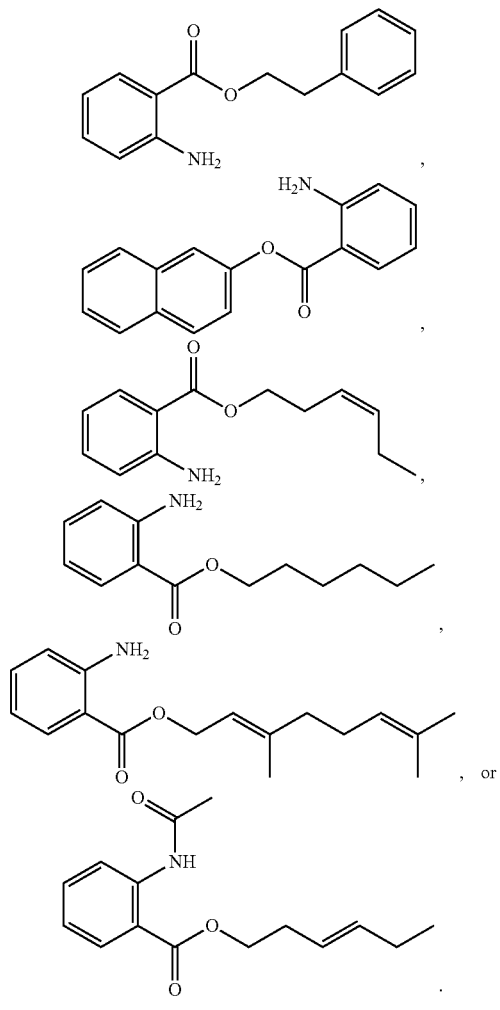

, or

5. The method of claim 1, wherein the at least one compound is

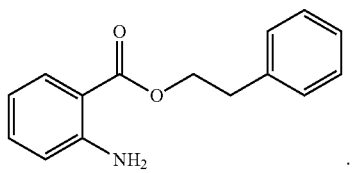 [SMILES: Nc1ccccc1C(=O)OCCc1ccccc1]

6. The method of claim 1, wherein the repelling composition is applied on the body of one or more vertebrates or one or more plants to expose the repelling composition to the arthropod.

7. The method of claim 1, wherein the repelling composition is formulated as a lotion, cream, dust, cosmetic, perfume, spray, paste, slow-release granule, paint, treated clothing, treated netting, treated building material, or incense.

8. The method of claim 1, wherein the exposing the arthropod to the repelling composition is carried out using a vaporizer, evaporator, fan, heat, candle, or wicked apparatus.

9. The method of claim 1, wherein the arthropod is of the order Diptera.

10. The method of claim 9, wherein the arthropod is of the genus *Drosophila*.

11. The method of claim 1, wherein the arthropod is a mosquito.

12. The method of claim 11, wherein the mosquito is of the species *Aedes aegypti*.

13. A method of repelling an arthropod, comprising exposing the arthropod to a repelling composition, wherein the repelling composition comprises at least one compound selected from the group consisting of:

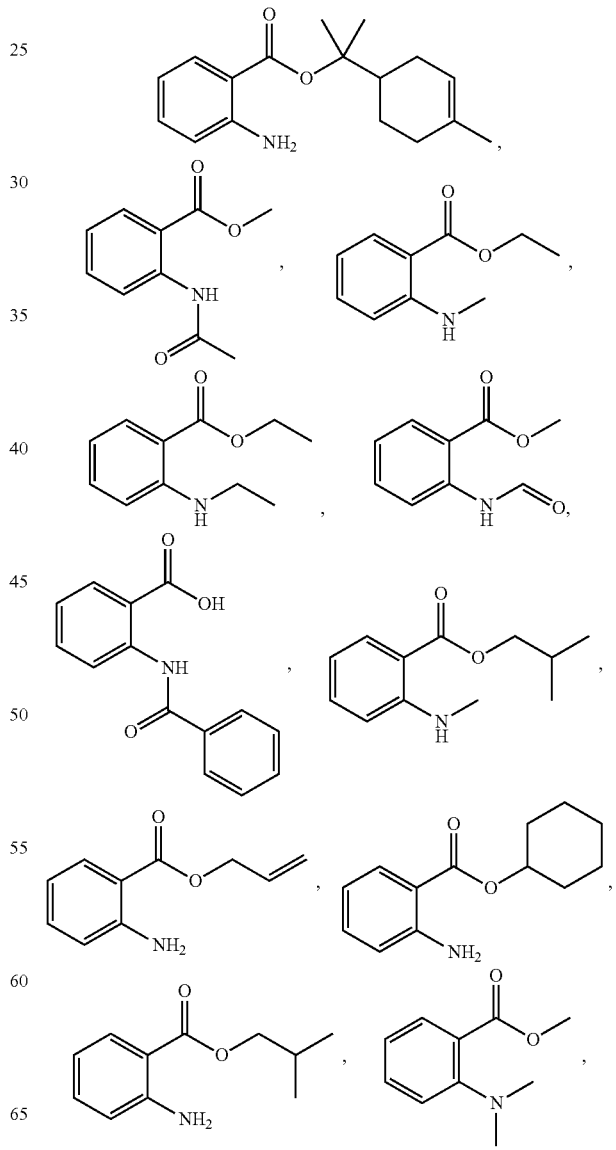

-continued
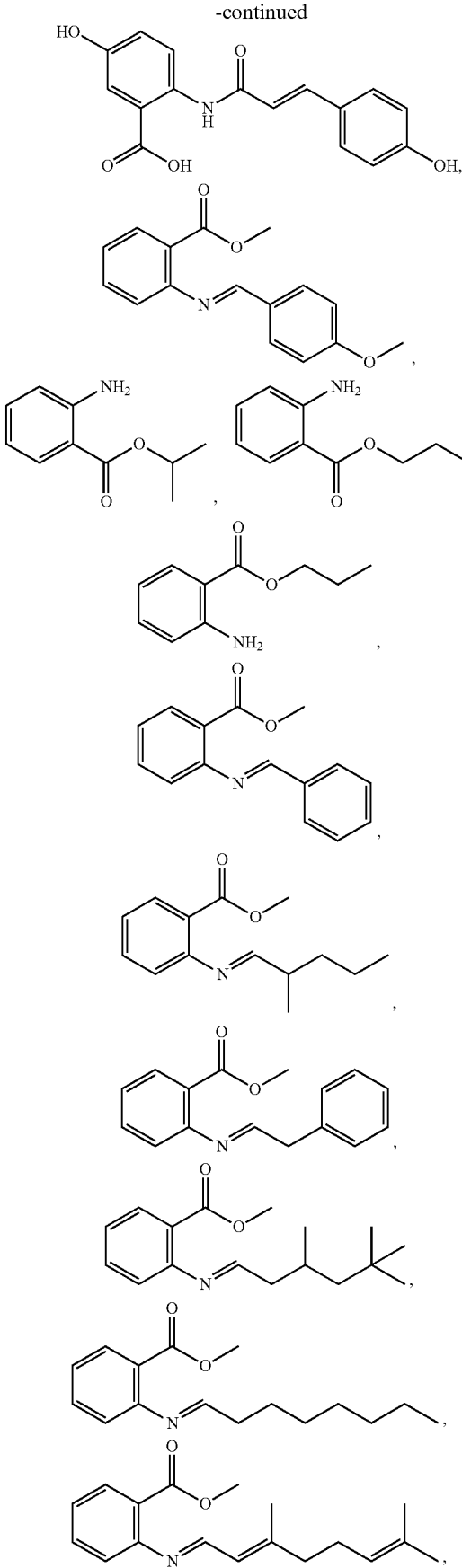
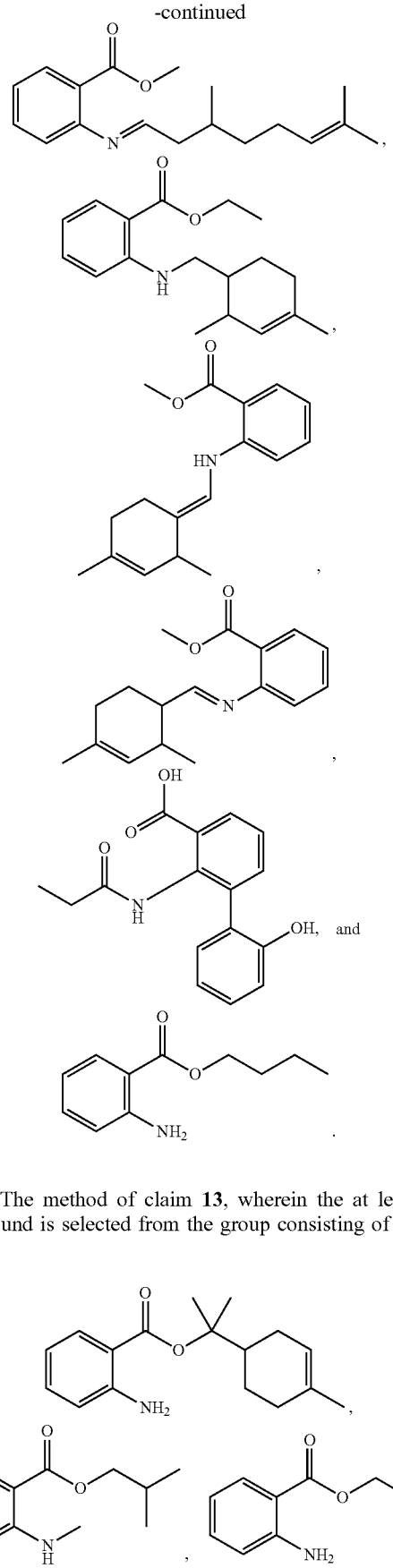
14. The method of claim 13, wherein the at least one compound is selected from the group consisting of -continued

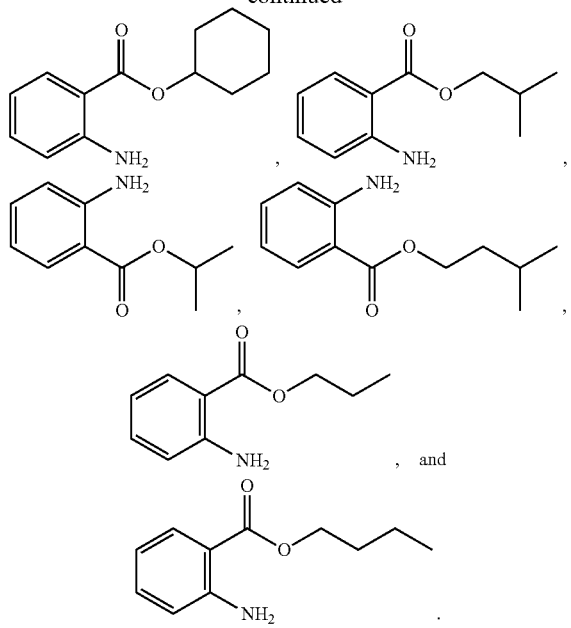

15. The method of claim 13, wherein the at least one compound is

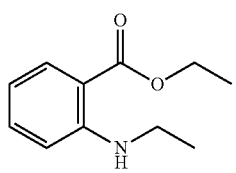

16. The method of claim 13, wherein the at least one compound is

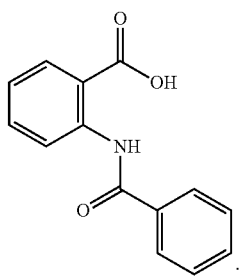 [SMILES: O=C(Nc1ccccc1C(=O)O)c1ccccc1]

17. The method of claim 13, wherein the at least one compound is

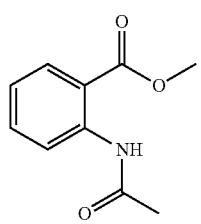

18. The method of claim 13, wherein the at least one compound is

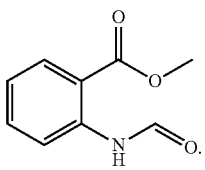

19. The method of claim 13, wherein the at least one compound is

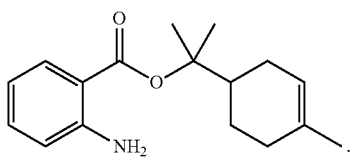 [SMILES: CC1=CCC(C(C)(C)OC(=O)c2ccccc2N)CC1]

20. The method of claim 13, wherein the at least one compound is

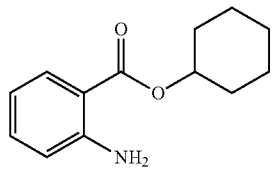

21. The method of claim 13, wherein the at least one compound is

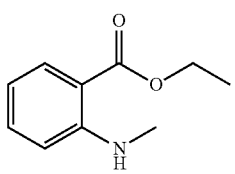

22. The method of claim 13, wherein the at least one compound is

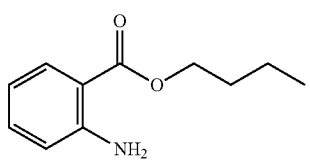

23. The method of claim 13, wherein the repelling composition is formulated as a lotion, cream, dust, cosmetic, perfume, spray, paste, slow-release granule, paint, treated clothing, treated netting, treated building material, or incense.

24. The method of claim 13, wherein the exposing the arthropod to the repelling composition is carried out using a vaporizer, evaporator, fan, heat, candle, or wicked apparatus.

25. The method of claim 13, wherein the arthropod is of the order Diptera.

26. The method of claim 25, wherein the arthropod is of the genus *Drosophila*.

27. The method of claim 13, wherein the arthropod is a mosquito.

28. The method of claim 27, wherein the mosquito is of the species *Aedes aegypti*.

* * * * *